(12) United States Patent
Herrell et al.

(10) Patent No.: US 10,238,457 B2
(45) Date of Patent: Mar. 26, 2019

(54) SYSTEM AND METHOD FOR ENDOSCOPIC DEPLOYMENT OF ROBOTIC CONCENTRIC TUBE MANIPULATORS FOR PERFORMING SURGERY

(71) Applicant: Vanderbilt University, Nashville, TN (US)

(72) Inventors: S. Duke Herrell, Nashville, TN (US); Robert J. Webster, III, Nashville, TN (US); Trevor Bruns, Nashville, TN (US); Philip J. Swaney, Nashville, TN (US); Richard Hendrick, Nasvhville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 738 days.

(21) Appl. No.: 14/256,540

(22) Filed: Apr. 18, 2014

(65) Prior Publication Data
US 2015/0080907 A1     Mar. 19, 2015

Related U.S. Application Data

(60) Provisional application No. 61/877,552, filed on Sep. 13, 2013.

(51) Int. Cl.
*A61B 1/00*     (2006.01)
*A61B 34/30*     (2016.01)
(Continued)

(52) U.S. Cl.
CPC .............. *A61B 34/30* (2016.02); *A61B 1/0016* (2013.01); *A61B 1/00087* (2013.01);
(Continued)

(58) Field of Classification Search
CPC ............ A61B 1/00131; A61B 1/00133; A61B 1/00135; A61B 1/00147; A61B 1/00149;
(Continued)

(56) References Cited

U.S. PATENT DOCUMENTS

2004/0138529 A1*   7/2004   Wiltshire ............. A61B 1/0055
                                                                                         600/144
2007/0060879 A1*   3/2007   Weitzner .......... A61B 17/12045
                                                                                         604/95.04

(Continued)

OTHER PUBLICATIONS

Wei, et al, "Performance Evaluation for Multi-Arm Manipulation of Hollow Suspended Organs" IEEE Transactions on Robotics, vol. 25, No. 1, Feb. 2009.
(Continued)

*Primary Examiner* — Ryan Henderson
(74) *Attorney, Agent, or Firm* — Tarolli, Sundheim, Covell & Tummino LLP

(57) ABSTRACT

An apparatus (20) for performing endoscopic surgery on a patient (12) includes at least two concentric tube manipulators (150) adapted to carry devices (152, 154) for performing a surgical operation. A transmission (200) operates the concentric tube manipulators (150). An endoscope tube (106) has a proximal end portion fixed to the transmission (200). The concentric tube manipulators (150) extend from the transmission (200) through an inner lumen (102) of the endoscope tube (106) and are operable to extend from a distal end (104) of the endoscope tube.

25 Claims, 11 Drawing Sheets

(51) Int. Cl.
| | |
|---|---|
| A61B 34/32 | (2016.01) |
| A61B 34/00 | (2016.01) |
| A61B 1/303 | (2006.01) |
| A61B 1/307 | (2006.01) |
| A61B 18/22 | (2006.01) |
| A61B 90/30 | (2016.01) |
| A61B 90/00 | (2016.01) |

(52) U.S. Cl.
CPC ...... *A61B 1/00131* (2013.01); *A61B 1/00133* (2013.01); *A61B 1/303* (2013.01); *A61B 1/307* (2013.01); *A61B 34/70* (2016.02); *A61B 34/72* (2016.02); *A61B 34/74* (2016.02); *A61B 18/22* (2013.01); *A61B 90/30* (2016.02); *A61B 90/361* (2016.02); *A61B 2034/301* (2016.02); *A61B 2034/742* (2016.02)

(58) Field of Classification Search
CPC ....... A61B 1/0016; A61B 34/00; A61B 34/30; A61B 34/32; A61B 34/35; A61B 34/37; A61B 34/70–34/77; A61B 2034/301–2034/306; A61B 2034/741–2034/744
USPC ..... 600/104, 106, 107, 114–116; 606/1, 130
See application file for complete search history.

(56) References Cited

U.S. PATENT DOCUMENTS

| | | | | |
|---|---|---|---|---|
| 2008/0243064 | A1* | 10/2008 | Stahler | A61B 34/71 604/95.01 |
| 2011/0015490 | A1* | 1/2011 | Trovato | A61B 17/3421 600/227 |
| 2011/0238083 | A1* | 9/2011 | Moll | A61B 34/20 606/130 |
| 2012/0071822 | A1* | 3/2012 | Romo | A61B 6/12 604/95.04 |
| 2012/0221011 | A1* | 8/2012 | Larkin | A61B 1/00087 606/108 |
| 2013/0035537 | A1* | 2/2013 | Wallace | A61B 34/30 600/8 |

OTHER PUBLICATIONS

Valdastri et al., "Advanced Technologies for Gastrointestinal Endoscopy" Annu. Rev. Biomed. Eng., vol. 14, pp. 397-429, 2012.
Valdastri et al., "Magnetic Air Capsule Robotic System: Proof of Concept of a Novel Approach to Painless Colonscopy" Sug. Endosc., vol. 26, pp. 1238-1246, 2012.
"Urinary Retention" National Kidney and Urological Diseases Information Clearinghouse, National Institutes of Health, NIH publication No. 08-6089, Dec. 2007.
Yu, et al., "Practice Patterns in Benign Prostatic Hyperplasia Surgical Therapy: The Dramatic Increase in Minimally Invasive Technologies" The Journal of Urology, vol. 180, pp. 241-245, Jul. 2008.
Trivedi et al., "Soft Robotics: Biological Inspiration, State of the Art, and Future Research" Applied Biomics and Biomechanics, vol. 5, No. 3, pp. 99-117, Sep. 2008.
Weinstein et al., "Transoral Robotic Surgery: Does the Ends Justify the Means?" Otolarngology & Head and Neck Surgery, vol. 17, pp. 126-131, 2009.
Burgner et al., "A Telerobotic System for Transnasal Surgery" IEEE/AMSE Transactions of Mechatronics, 2013.
Swaney et al., "Design of a Quadramanual Robot for Single-Nostrik Skull Base Surgery" ASME 2012 5th Annual Dynamic Systems and Control Conference joint with JSME 2012 11th Motion and Vibration Conference, Fort Lauderdale, FL, Oct. 17-19, 2012.
Goldman et al., "Design and Performance Evaluation of a Minimally Invasive Telerobotic Platform for Transurethral Survelliance and Intervention", IEEE Transactions on Biomedical Engineering, vol. 60, No. 4, Apr. 2013.

Simaan et al., "Design and Integration of a Telerobotic System for Minimally Invasive Surgery of the Throat" The International Journal of Robotics Research, vol. 28, No. 9, pp. 1134-1153, Sep. 2009.
Bajo et al., "Constrained Motion Control of Multisegment Continuum Robots for Transurethral Bladder Resection and Surveillance" IEEE International Conference on Robotics and Automation, Karisruhe, Germany,May 2013.
Shoham, et al., "Bone-Mounted Miniature Robot for Surgical Procedures: Concept and Clinical Applications" IEEE Transactions on Robotics and Automation, vol. 19, No. 5, Oct. 2003.
Shang et al., "An Articulated Universal Joint Based Flexible Access for Robot for Minimally Invasive Surgery" IEEE International Conference on Robotics and Automation, Shanghai International Conference Center, 2011.
Schurizig et al., "A Force Sensing Automated Insertion Tool for cochlear Electrode Implantation" IEEE International Conference on Robotics and Automation, Anchorage, Convention District, 2010.
Rucker et al., "A Geometrically Exact Model for Externally Loaded Concentric-Tube Continuum Robots" IEEE Transactions on Robotics, vol. 26, No. 5, Oct. 2010.
Rucker, and Webster III, "Statics and Dynamics of Continuum Robots with General Tendon Routing and External Loading" IEEE Transactions on Robotics, vol. 27, No. 6, Dec. 2011.
Rucker, and Webster III, "Computing Jacobians and Compliance Matrices for Externally Loaded Continuum Robots" IEEE International Conference on Robots and Automation, Shanghai International Conference Center, May 2011.
Burgner et al., "A Bimanual Telepoerated System for Endonasal Skull Base Surgery" IEEE/RSJ International Conference on Intelligent Robots and Systems, San Franscisco, CA, Sep. 2011.
Miroir et al., "RobOtol: From Design to Evaluation of a Robot for the Middle Ear Surgery" IEEE/RSJ International Conference on Intelligent Robots and Systems, Taipei, Taiwan, Oct. 2010.
Davies et al., "The Development of a Surgeon Robot for Prostatectomies" Pros. Instn Mech Engrs. vol. 205, 1991.
Harris et al., "The Probot—an Active Robot for Prostate Resection" Pros Instn Mech Engrs, vol. 211, Part H, 1997.
Okazawa et al., "Hand-Held Steerable Needle Device" IEE/ASME Transactions on Mechanics, vol. 10, No. 3, Jun. 2005.
McConnell et al., "The Long-Term Effect of Doxazosin, Finasteride, and Combination Therapy on the Clinical Progreession of Benign Prostatic Hyperplasia" The New England Journal of Medicine, vol. 349 No. 25, Dec. 2003.
Kuo et al., "Holmium Laser Enucleation of the Prostate (HoLEP): A Technical Update" World Journal of Surgical Oncology, vol. 1, No. 6, 2003.
Lingeman, "Holium Laser Enucleation of the Prostate—If Not Now, When?" The Journal of Urology, vol. 186, 2011.
Mandeville et al., "New Advances in Benign Prostatic Hyperplasia: Laser Therapy" Curr Urol Rep, vol. 12, 2011.
Gnessin et al., "An Updated on Holmium Laser Enucleation of the Prostate and why it has Stood the Test of Time" Current Opinion in Urology, 2011.
Abraham et al., "Years Lived with Disability (YLDs) for 1160 Sequelae of 289 Diseases and Injuries 1999-2010: A Systematic Analysis of the Global Burden of Disease Study 2010" Lancet, 2012.
Ahyai, et al., "Holmium Laser Enucleation Versus Transurethral Resection of the Prostate: 3-Year Follow-Up Results of a Randomized Clinical Trial" European Association of Urology, 2007.
Matinfar et al., "Robot-Assisted Skull Base Surgery" 2007 IEEE/ RSJ International Conference on the Intelligent Robots and Systems, San Diego, Ca, 2007.
Issa et al., "An Assessment of the Diagnosed Prevalence of Disease in Men 50 Years of Age or Older" The American Journal of Managed Care, vol. 14, No. 4.
Seki and Naito, "Holmium Laser for Benign Prostate Hyperplasia" Current Opinion in Urology, 2008.
Mavudura et al., "Comparison of HoLEP and TURP in Terms of Efficacy in the Early Postoperative Period and Perioperative Morbidity" Urologia Internationalis, 2007.

(56) References Cited

OTHER PUBLICATIONS

Tooher, et al., "A Systematic Review of Holmium Laser Prostatectomy for Benign Prostatic Hyperplasia" The Journal of Urology, vol. 171, 2004.

"HoLEP an Option After Failed Prior BPH Surgery", Chicago.

Hashimoto et al., "A Tubular Organ Resection Manipulator for Transurethral Resection of the Prostate" IEEE/RSJ International Conference on Intelligent Robots and Systems, 2004.

Guess et al., "Cumlative Prevalence of Prostatism Matches the Autopsy Prevalence of Benign Prostatic Hyperplasia" The Prostate, vol. 17, 1990.

Focacci, et al., "Lightweight Hand-Held Robot for Laparoscopic Surgery" IEEE International Conference on Robotics and Automation, Rome, Italy, 2007.

Fenter et al., "The Cost of Treating the 10 Most Prevalent Diseases in Men 50 Years of Age or Older" The American Journal of Managed Care, 2006.

Emberton et al., "Benign Prostate Hyperplasia: A Progressive Disease of Aging Men" Elsevier Science, Inc., Urology, vol. 61, 2003.

Saigal and Joyce, "Economic Costs of Benign Prostatic Hyperplasia in the Private Sector" The Journal of Urology, vol. 173, 2005.

Dupont et al., "Design and Control of Concentric-Tube Robots" IEEE Transactions on Robotics, vol. 26, No. 2, 2010.

Dario, et al., "A Novel Mechatronic Tool for Computer-Assisted Arthroscopy" IEEE Transactions on Information Technology in Biomedicine, vol. 4, No. 1, 2000.

Chiaverini, "Singularity-Robust Task-Priority Redundancy Resolution for Real-Time Kinematic Control of Robot Manipulators" IEEE Transactins on Robotics and Automation, vol. 13, No. 3, 1997.

Butler et al., "Robotic Neuro-Endoscope with Concentric Tube Augmentation" IEEE/RSJ International Conference on Intelligent Robots and Sytems, Portugal, 2012.

Burke et al., "Systematic Review and Meta-Analysis of Transurethral Resection of the Prostate Versus Minimally Invasive Procedures for the Treatment of Bengin Prostatic Obstruction" J. Urology, 2009.

Burgner et al., "Debulking from Within: A Robotic Steerable Cannula for Interacerebral Hemmorage Evacuation" IEEE Transactions on Biomedical Engineering, vol. 60, No. 9, 2013.

Burgner et al., "A Telerobotic System for Transnasal Surgery" IEEE/ASM Transactions on Mechatronics, 2013.

Wei et al., "Urologic Diseases in America Project: Benign Prostatic Hyperplasia" The Journal of Urology, vol. 173, 2005.

Kruep et al., "Evaluation of Recent Trends in Treatment Patterns Among Men with Benign Prostatic Hyperplasia" American Journal of Men's Health, http://jmh.sagepub.com/content/7/3/214.

Wampler, II, "Manipulator Inverse Kinematic Solutions Based on Vector Formulations and Damped Least-Squares Methods" IEEE Transactions on Systems, Man and Cybernetics, vol. SMC-16, No. 1 1986.

Yamashita et al., "Handheld Laparoscopis Forceps Manipulator Using Multi-Slider Linkage Mechanisms" MICCAI 2004.

\* cited by examiner

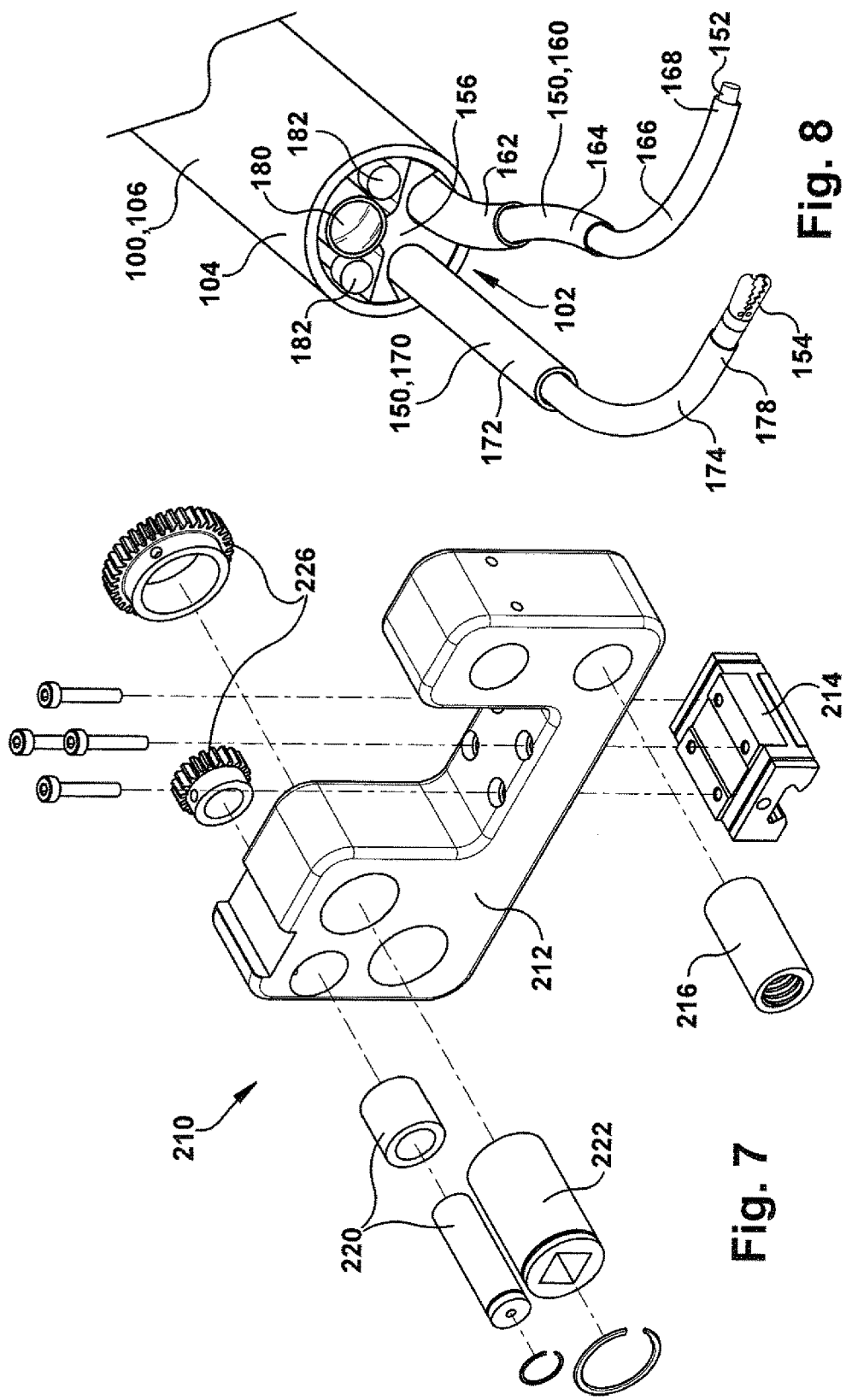

SYSTEM AND METHOD FOR ENDOSCOPIC DEPLOYMENT OF ROBOTIC CONCENTRIC TUBE MANIPULATORS FOR PERFORMING SURGERY

RELATED APPLICATION

This application claims the benefit of U.S. Provisional Application Ser. No. 61/877,552, which was filed on Sep. 13, 2013.

GOVERNMENT RIGHTS

This invention was made with government support under National Science Foundation Career Award Grant No. IIS-105433, and under National Institutes of Health Grant No. R01 EB017467. The government has certain rights in the invention.

TECHNICAL FIELD

The invention relates to surgical robots. In one particular implementation, the invention relates to a system and apparatus for the endoscopic deployment of robotically controlled concentric tube manipulators for performing surgery.

BACKGROUND

Recent advances in surgical robotics are enabling less invasive access to the human body through natural orifices. Transoral surgery has been an approach of substantial recent interest, perhaps since the mouth is the largest natural orifice. Many in the surgical community have focused on using Intuitive Surgical, Inc.'s da Vinci™ Surgical System robot for this purpose, while engineering interest has focused on custom designed robot solutions. There has been a recent progression in the surgical robotics community toward designing robots to work through ever smaller orifices. Numerous systems have been designed for colorectal inspection and surgery. Recently, teleoperated and/or cooperative systems have been developed for ear surgery, endonasal surgery, and transurethral bladder surgery. Yet despite the relatively small diameter of the urethra, it is also interesting to note that transurethral surgery was actually one of the earliest surgical robotics applications.

Benign prostatic hyperplasia (BPH), or enlargement of the prostate, is the most prevalent symptomatic disease in men, occurring in 8% of men in their 30s, 50% in their 50s, and 90% in their 80s. BPH occurs when the prostate grows large enough that it restricts the flow of urine through the urethra, which passes through the prostate. The goal of a surgical intervention for BPH is to remove prostate tissue surrounding the urethra and thereby enable normal urine flow to resume. Transurethral resection of the prostate (TURP) is the current standard surgical approach for BPH. It is accomplished endoscopically, through the urethra, and prostate tissue is removed in pieces by either sharp dissection or electrocautery. Although the approach to the prostate is minimally invasive, the tools used to remove tissue can cause substantial bleeding (potentially requiring transfusion), long catheterization time, urethral narrowing, and bladder neck narrowing.

Holmium Laser Enucleation of the Prostate (HoLEP) is another surgical procedure for treating BPH. HoLEP can alleviate many of these concerns, since the Holmium laser provides an ideal combination of cutting and coagulation. HoLEP enables dissection without significant thermal spread (making HoLEP safer than electrocautery for nearby structures such as nerves), and without substantial blood loss. The reduction in morbidity in HoLEP compared to TURP has been corroborated in a number of clinical studies. These show that HoLEP reduces average catheterization time (2 days to 1 day), hospital stay (3 days to 2 days), and blood loss (eliminates the need for transfusions). The improvement in outcomes is sufficiently compelling that HoLEP is now generally viewed in the urology community as the superior treatment.

In spite of this, HoLEP adoption has been slow, and it is currently only conducted in relatively few institutions in the USA compared to TURP, which was conducted approximately 50,000 times in the United States in 2005. The best explanation for why HoLEP has not been more widely adopted is that it is extremely challenging for the surgeon. The challenge is brought about due to the fact that the laser proceeds straight out of the endoscope and can only be aimed by moving the entire endoscope. Since the endoscope must pass through a great deal of soft tissue on the way to the prostate, its maneuverability is limited. Large forces are required to aim the endoscope and the only way to physically manipulate tissue near its tip is to use the tip of the endoscope itself. It is challenging and physically demanding for surgeons to attempt to accurately aim the laser using the endoscope while simultaneously applying large forces to the same endoscope to deform the tissue.

SUMMARY

The invention relates to a robotic system, method, and apparatus for performing endoscopic surgery. The endoscopic approach can implement a rigid or flexible endoscope to access a target surgical site through a port in the body. These ports can be natural orifices (e.g., mouth, nose, ears, rectum, urethra) or incisions (e.g., chest, abdomen, head). In one implementation, the invention relates to a robotic surgical system that deploys two or more robotic concentric tube manipulators through an endoscope.

In one implementation, the robotic surgical system is used to perform transurethral surgery that focuses on the prostate. In this implementation, the robotic surgical system is used to perform a transurethral Holmium Laser Enucleation of the Prostate (HoLEP), which is useful in the management of Benign Prostatic Hyperplasia (BPH). According to one aspect, the robot is adapted for both manual and robotic operation.

According to this aspect, a robotic system deploys one or more concentric tube manipulators, at least one of which includes a HoLEP laser, through a conventional endoscope or endoscope tube that is fit with a video camera and an illumination source for facilitating remote viewing. Through this system, the surgeon can manually manipulate the endoscope, which is inserted into the urethra, to place its distal end at a desired location relative to the target. Once positioned, the surgeon can use the concentric tube manipulators to perform the operation. In one particular configuration, the system includes two concentric tube manipulators—one carrying a HoLEP laser and the other carrying a gripper that allows for manipulating tissue, exposing areas for laser dissection, and removing dissected tissues from the patient's body.

Through this operation, the surgeon can control gross motions of the endoscope manually in the usual accustomed manner, while fine motions of the concentric tube manipulators at the endoscope tip are accomplished via controller interface devices, such as thumb joysticks and finger triggers located near the surgeon's hands. The surgeon can view the endoscope image on a screen, which can be positioned on the back of the robot unit or on a display screen in the operating room.

Advantageously, the endoscope that passes into the patient is of the same diameter as that currently used clinically for HoLEP procedures. According to one aspect of the invention, the endoscope advantageously permits delivery of the optics for the camera, the light sources, a concentric tube manipulator carrying the Holmium laser fibers, and a concentric tube manipulator carrying the manipulators, while leaving room for injecting and suctioning irrigation fluids.

According to one aspect of the invention, an apparatus for performing endoscopic surgery on a patient includes at least two concentric tube manipulators adapted to carry devices for performing a surgical operation. A transmission operates the concentric tube manipulators. An endoscope tube has a proximal end portion fixed to the transmission. The concentric tube manipulators extend from the transmission through an inner lumen of the endoscope tube and are operable to extend from a distal end of the endoscope tube.

According to another aspect of the invention, an apparatus for performing endoscopic surgery on a patient includes an endoscope tube and two or more concentric tube manipulators positioned in an inner lumen of the endoscope tube. The endoscope tube is configured to be delivered transurethrally to a worksite in the patient.

DESCRIPTION OF DRAWINGS

FIG. 7 is an exploded isometric view of a portion of the robot illustrated in FIGS. 2-6.

FIG. 8 is a magnified isometric view of a portion of the robot illustrated in FIGS. 2-7.

DESCRIPTION

The Surgical System

Figure 1:
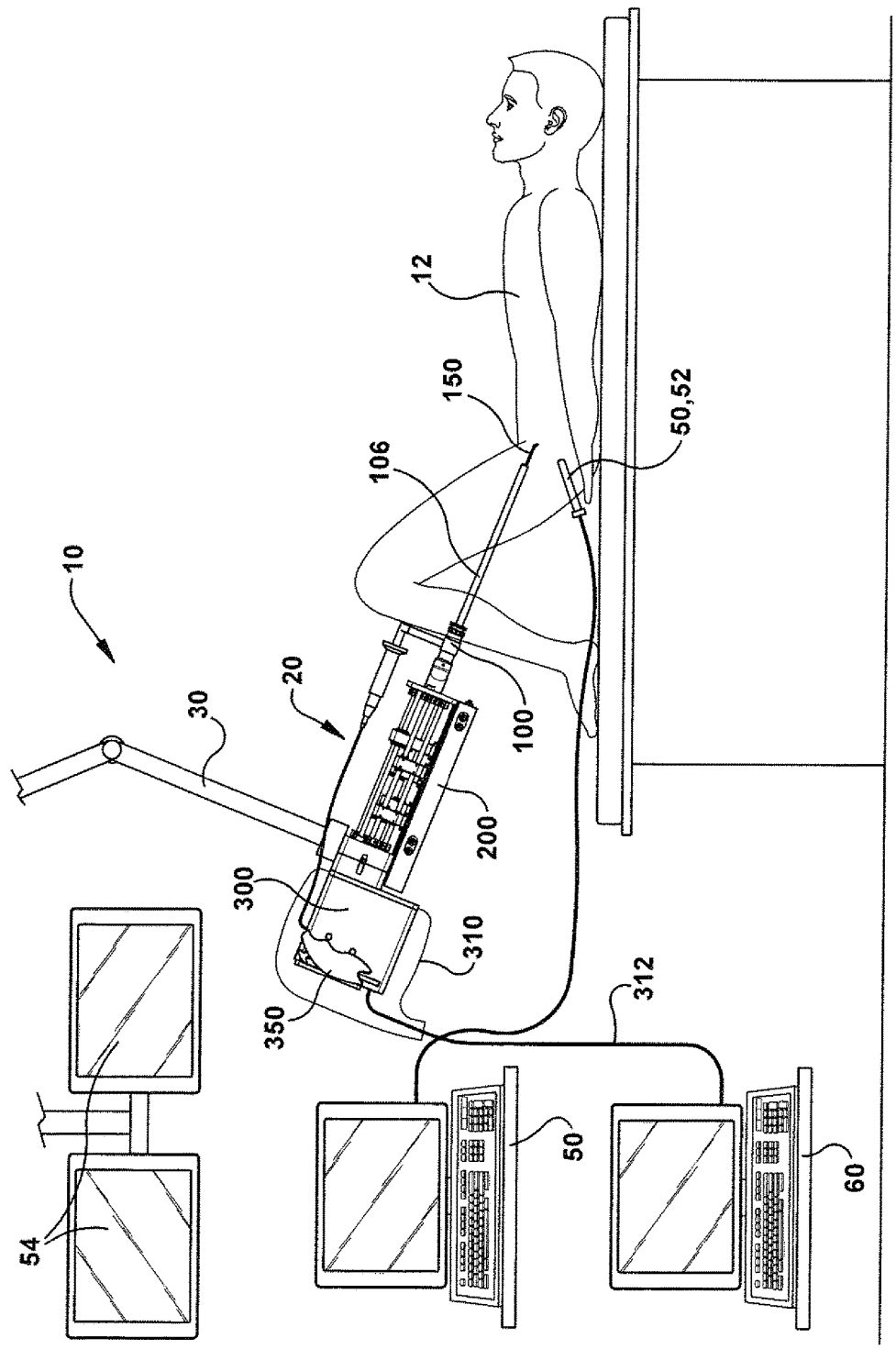
FIG. 1 illustrates a system and apparatus for the endoscopic deployment of robotically controlled concentric tube manipulators for performing surgery, according to an aspect of the invention.
Figure 2:
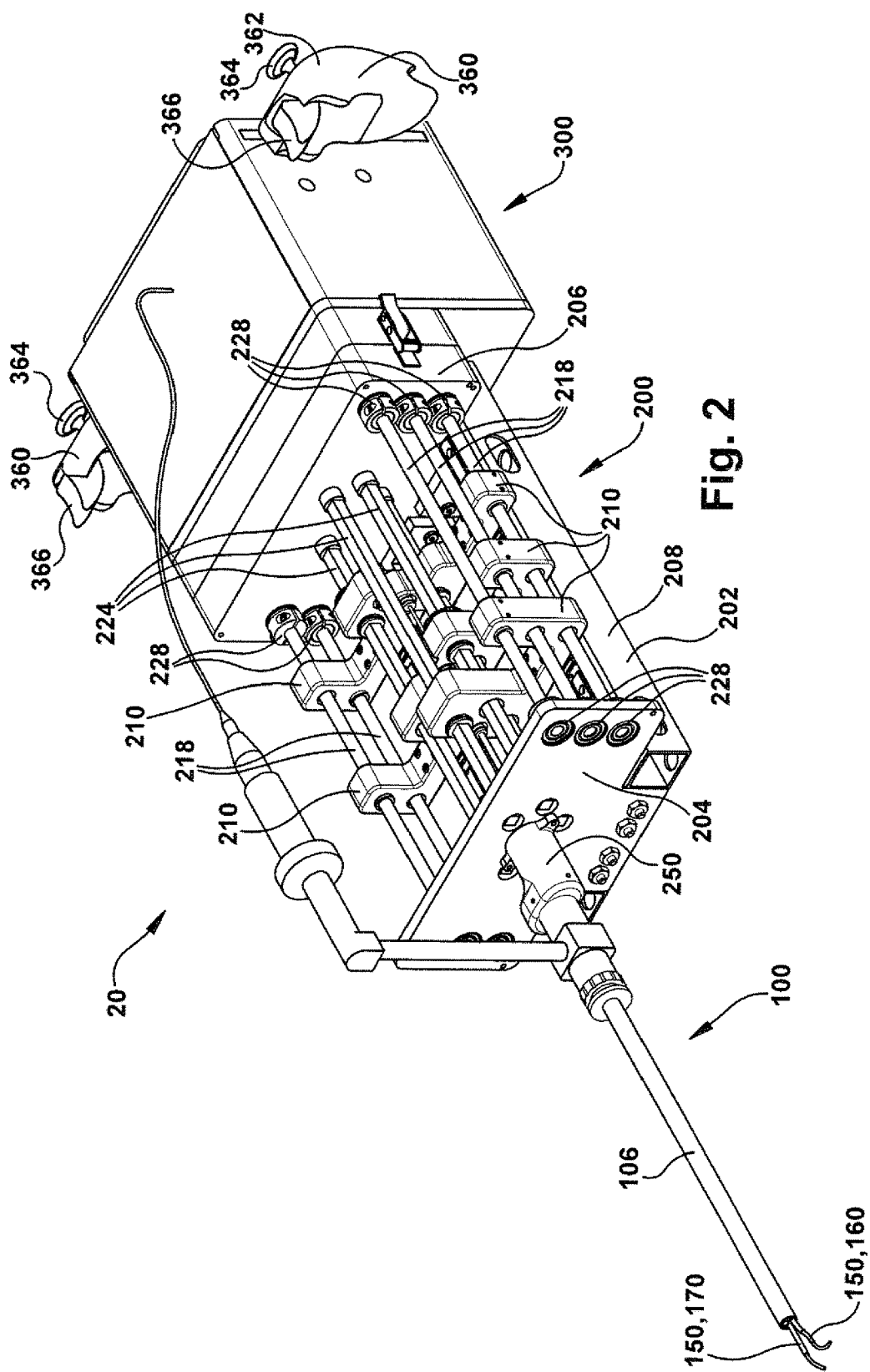
FIGS. 2 and 3 are isometric views of a robot that forms a portion of the system and apparatus illustrated in FIG. 1.
Figure 3:
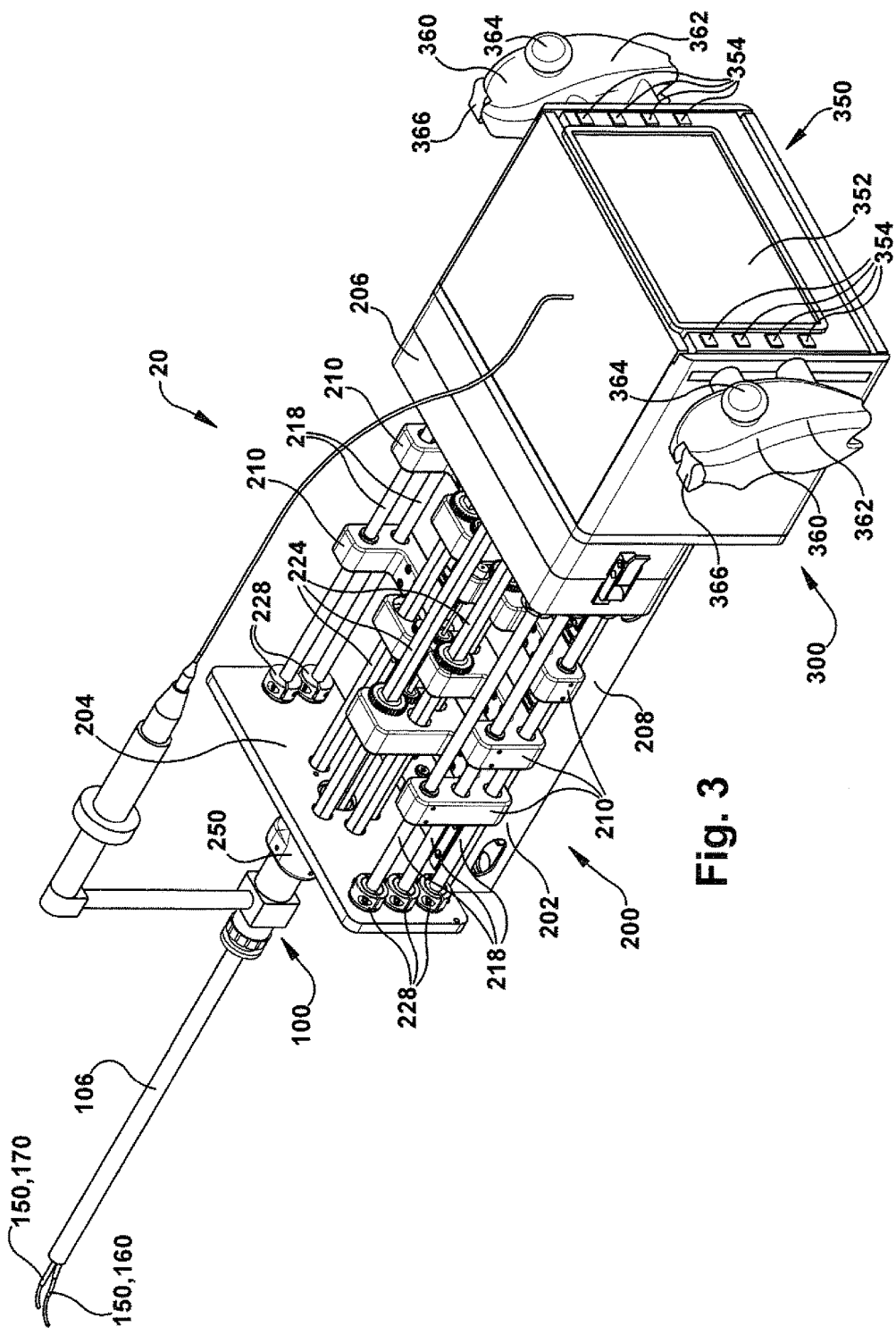
Figure 4:
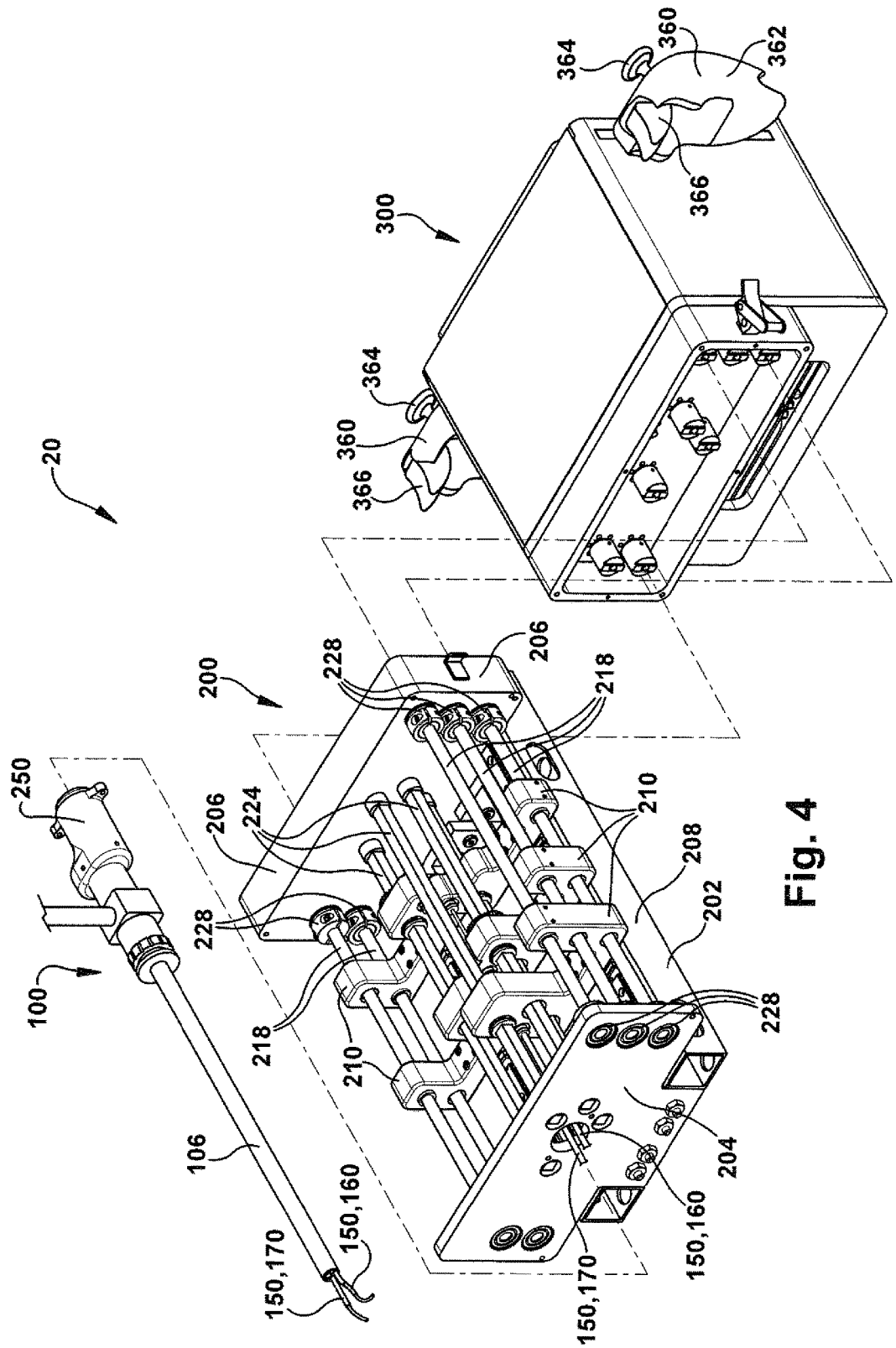
FIG. 4 is an exploded isometric view of the robot illustrated in FIGS. 2 and 3.
Figure 5:
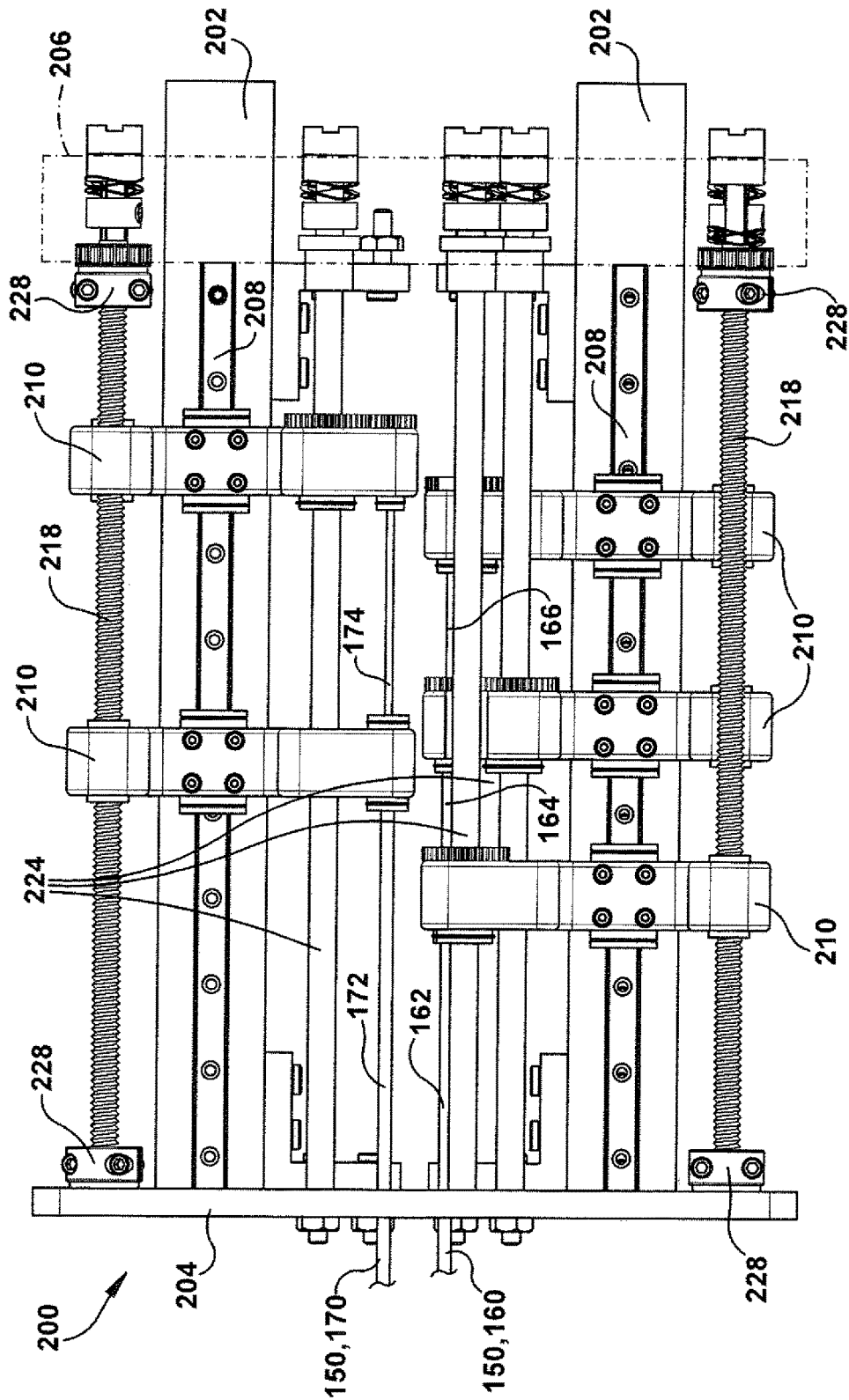
FIGS. 5 and 6 are top plan and side elevation views, respectively, of the robot illustrated in FIGS. 2-4.
Figure 6:
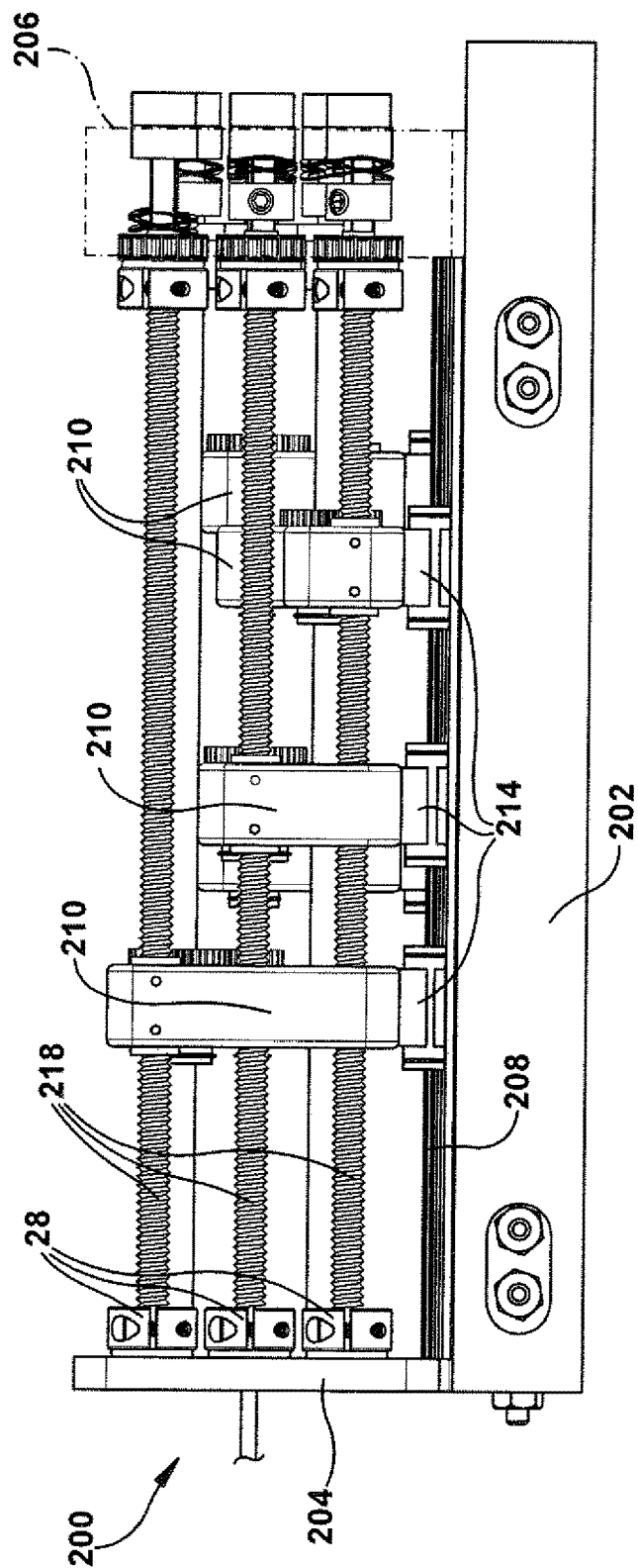

FIG. 1 illustrates an operating room environment in which surgery can be performed. Referring to FIG. 1, a system 10 for performing surgery on a patient 12 includes an apparatus 20 in the form of a robot. The robot 20 includes an endoscope 100 that includes an endoscope tube 106 through which one or more concentric tube manipulators 150, which can also be referred to as "active cannulas" or "concentric tube robots" extend. The robot 20 could include more than two concentric tube manipulators 150. The robot 20 also includes a transmission 200 for manipulating the operation of the concentric tube manipulators 150, and a motor pack 300 that includes user interface and control features.

The endoscope 100 is releasably connected to a front or distal end of the transmission 200 and the motor pack 300 is releasably connected to a proximal end of the transmission. The robot 20 is supported on a support device, which is illustrated generally at 30. The support device 30 permits the user (i.e., surgeon) to easily maneuver and position the robot 20. To achieve this, the support device 30 can be configured (e.g., counterbalanced) so as to negate all or a portion of the weight of the robot 20. The support device 30 can also have locking features that allow the user to fix the position of the robot 20 so that the user can focus on manipulating the concentric tube manipulators 150 via the user interface and control features 350. The robot 20 can be connected via cable(s) 312 to a robot interface PC 60 that is used to help program, control, and monitor the operation of the robot 20.

An imaging guidance system 50, such as an ultrasound system, can be used to aid the user in guiding the robot 20 in the patient 12. For instance, in an implementation where the system 10 is used to treat BPH, the endoscope can enter the patient 12 via a transurethral insertion and an ultrasound probe 52 can be inserted anally to a position in the vicinity of the prostate. The image guidance can be viewed via the image guidance system 50 itself, or on monitors 54 mounted in the operating room. The monitors 54 can also be used to view video images obtained via the robot 20.

The Robot—Concentric Tube Manipulators

Referring to FIG. 8, the concentric tube manipulators 150 are small, needle-diameter, tentacle-like robots that include multiple concentric, precurved, elastic tubes. These elastic, curved tubes are typically made of a superelastic metal alloy such as a nickel-titanium alloy ("nitinol") material. The tubes can, individually or in combination, be rotated about the longitudinal axis of the robot and can be translated along the longitudinal axis of the robot. Through translational movement, the tubes can be retracted into one another and extended from one another.

As the precurved tubes interact with one another through relative translational and rotational movement, they cause one another to bend and twist, with the tubes collectively assuming a minimum energy conformation. The precurvature(s) of the tube(s) for a given manipulator 150 can be selected to provide a desired workspace throughout which the tip can access. The curved shape of the distal end of the manipulator 150 is controlled via translation and rotation of each tube at a proximal location (e.g., at its base) outside the patient. The concentric tube manipulators 150 are particularly well suited to natural orifice procedures because their small diameter and remote actuation enable them to operate in areas where bulkier actuation systems (e.g., tendons and pulleys) are not feasible. The size of the manipulator 150 is limited only by the size of nitinol tubes available, which can be an outer diameter of as little as 200 μm or less.

In the embodiment illustrated in FIG. 8, the robot 20 includes two concentric tube manipulators 150 positioned in the inner lumen 102 of the endoscope tube 106 and are actuatable to protrude from the distal end 104 of the endoscope 100. Distal ends of the manipulators 150 carry surgical tools, such as a Holmium laser fiber 152 and grippers 154. The manipulators 150 could carry alternative tools, such as surgical lasers, graspers, retractors, scissors, imaging tips (e.g., endomicroscopy, optical coherence tomography (OCT), spectroscopy), cauterization tips, ablation tips, wrists (for dexterity), curettes, morcelators, knives/scalpels, cameras, irrigation ports, and suction ports. A spacer 156 positioned in the lumen 102 guides the manipulators 150 so their operations don't interfere with each other. The spacer 156 can be fixed in the lumen 102 of the endoscope 100 by means, such as friction or an adhesive.

A first concentric tube manipulator 160 includes three concentric tubes: an outer tube 162, a first inner tube 164, and a second, or innermost, inner tube 166 with a tip 168 that carries the laser fiber 152. A second concentric tube manipulator 170 includes two concentric tubes: an outer tube 172 and an inner tube 174 with a tip 178 that carries the grippers 154.

According to one aspect of the invention and in one particular implementation, the outer tube 172 can be a straight, stiff tube made, for example, of stainless steel. In this configuration, the straight outer tube 172 can be relatively rigid so that the curved inner tube 174 that it carries will conform and straighten when retracted therein. The concentric tube manipulator 170 thus has three degrees of freedom (DOF), i.e., the outer tube 172 can translate axially and the inner tube 174 can translate axially and also rotate. Additionally, according to this aspect, all three tubes 162, 164, 166 of the concentric tube manipulator 160 can be curved, and each can have two degrees of freedom, i.e., each can translate axially and also rotate. The six DOF manipulator 160 and the three DOF manipulator 170 in combination provide a nine DOF robot 20. The degrees of freedom of the robot 20 can be adjusted or re-configured by adjusting the number concentric tube manipulators 150, the number of concentric tubes in each manipulator, or the curved configurations of the concentric tubes.

In describing the unique characteristics of the curved concentric tube manipulators 150 described herein, it should be noted and understood what is meant by the terms "axis" or "axial" used in conjunction with the manipulators. Because the curved tubes are coaxial in nature, the axis of the manipulators 150 themselves can be considered to be centered within and follow the curved configuration of the manipulators. Thus, as the curved configuration of the manipulator 150 changes, the axis remains centered in the tubes and follows. However, in this description, reference is also made to rotation of the manipulators 150 and to rotation of the individual concentric tubes that make up the manipulators. In this description, rotation of the manipulators 150 or of any of the concentric tubes that make up the manipulators is meant to refer to rotation about a straight portion of the manipulator that extends through the endoscope 100. Thus, as the manipulator 150 rotates, the straight portions of the concentric tubes within the endoscope 100 rotate about a common central axis (i.e., coaxially) whereas the curved portions of the tubes outside the endoscope move about that same straight linear axis.

The inner tubes 164, 166, 174 when extended from within the outer tubes 162, 172 will resume their precurved configurations due to their superelastic material construction. By controlling the relative translational and rotational positions of their respective tubes, the tips 168, 178 can be maneuvered to any position within the workspace defined by the characteristics of the particular tubes. Thus, through careful selection of the tubes used to construct the manipulators 160, 170, their respective workspaces can be tailored to suit the particular surgical task and the physiology of the patient environment in which the task is performed.

The Robot—Transmission

Referring to FIGS. 2-6, the transmission 200 of the robot 20 includes a frame 202 that supports a front end plate 204 and a rear motor interface housing 206. The frame 202 includes a pair of rails 208 that extend between and interconnect the end plate 204 and the motor interface housing 206. The end plate 204 and a motor interface housing 206 include bearings 228 that receive opposite ends of a plurality of threaded drive screws 218 and rotation shafts 224. The bearings 228 support the screws 218 and shafts 224 and facilitate their rotation.

The transmission 200 also includes a plurality of tube carriers 210, each of which is supported on one of the rails 208 and is movable longitudinally along its associated rail. The transmission 200 includes one tube carrier for each individual tube of the manipulators 150. Thus, for the nine DOF, two manipulator example configuration of the robot 20 illustrated herein, there are five tube carriers 210—three associated with the first manipulator 160 and two associated with the second manipulator 170.

Referring to FIG. 7, each tube carrier 210 includes a frame 212 and a bearing block 214 that interfaces with its associated rail 208 to facilitate its longitudinal movement thereon. As shown in FIG. 7, the bearing block 214 can have a downward facing recess with a trapezoidal configuration that mates with a corresponding configuration of a mating portion of the rail 208 upon which it slides. The bearing block 214 can include bearing elements, such as balls or rollers, for facilitating sliding along the rails 208. In one example configuration, the bearing block 214 and rails 208 could be those commercially available from THK America, Inc. of Schaumburg, Ill., part number HSR8R, which can sustain significant moment loads while continuing to slide freely.

Each tube carrier 210 also includes a lead nut 216 for receiving one of the threaded drive screws 218 (see FIGS. 2-6). The lead nut 216 includes internal screw threads that mate with external screw threads on its associated drive screw 218. Rotation of the drive screw 218 thus can impart movement of the tube carrier 210 and along its associated rail 208. Rotation of the drive screw 218 in one direction imparts movement of the tube carrier 210 in a first longitudinal direction (e.g., an insertion direction); and rotation of the drive screw in the opposite direction imparts movement of the tube carrier in a second opposite longitudinal direction (e.g., a retraction direction).

Each tube carrier 210 also includes a tube holder 220 for supporting a tube of the associated concentric tube manipulator 150. The tube holder 220 is configured for rotation relative to the tube carrier 210 via a bearing structure. The tube holder 220 is also configured to grasp or otherwise support the associated tube so that the tube can rotate relative to the carrier 210 with the tube holder, but is not permitted to move longitudinally relative to the carrier. Thus, the tube holder 220 is configured such that the tube can rotate relative to the tube carrier 210 and such that the tube translates longitudinally with the tube carrier.

Each tube carrier 210 also includes a sleeve 222 with a central bore for receiving an associated rotation shaft 224 (see FIGS. 2-6). The sleeve 222 is configured to permit the shaft 224 to slide freely through the bore so that the tube carrier 210 can slide freely along its associated rail 208. The central bore of the sleeve 222 has a configuration (e.g., square in the illustrated embodiment) that mates with the cross-sectional shape of the rotation shaft 224 so that rotation of the shaft imparts rotation of the sleeve.

Each tube carrier 210 further includes a gear train 226 including a primary gear mounted for rotation with the sleeve 222 and a secondary gear mounted for rotation with the tube holder 220. The tube carrier 210 is thus configured such that rotation of the rotation shaft 224 imparts rotation of the tube holder 220 via the gear train 226. The rotation shaft 224 is thus configured to impart rotation to the manipulator tube of the associated tube holder 220.

From the above description, it will be appreciated that each tube carrier 210 is configured to impart translational movement of its associated manipulator tube via rotation of the associated drive screw 218, and to impart rotational movement of its associated manipulator tube via rotation of the associated rotation shaft 224. For translational movement, the tube carrier 210 moves linearly along the length of the transmission frame 202, driven by the drive screw 218 to travel along its respective rail 208, and carrying with it the associated manipulator tube. For rotational movement, the tube holder 220 rotates within the tube carrier 210, driven by the rotation shaft 224 via the gear train 226, and the associated manipulator tube rotates with it.

The Robot—Motor Pack

Figure 10:
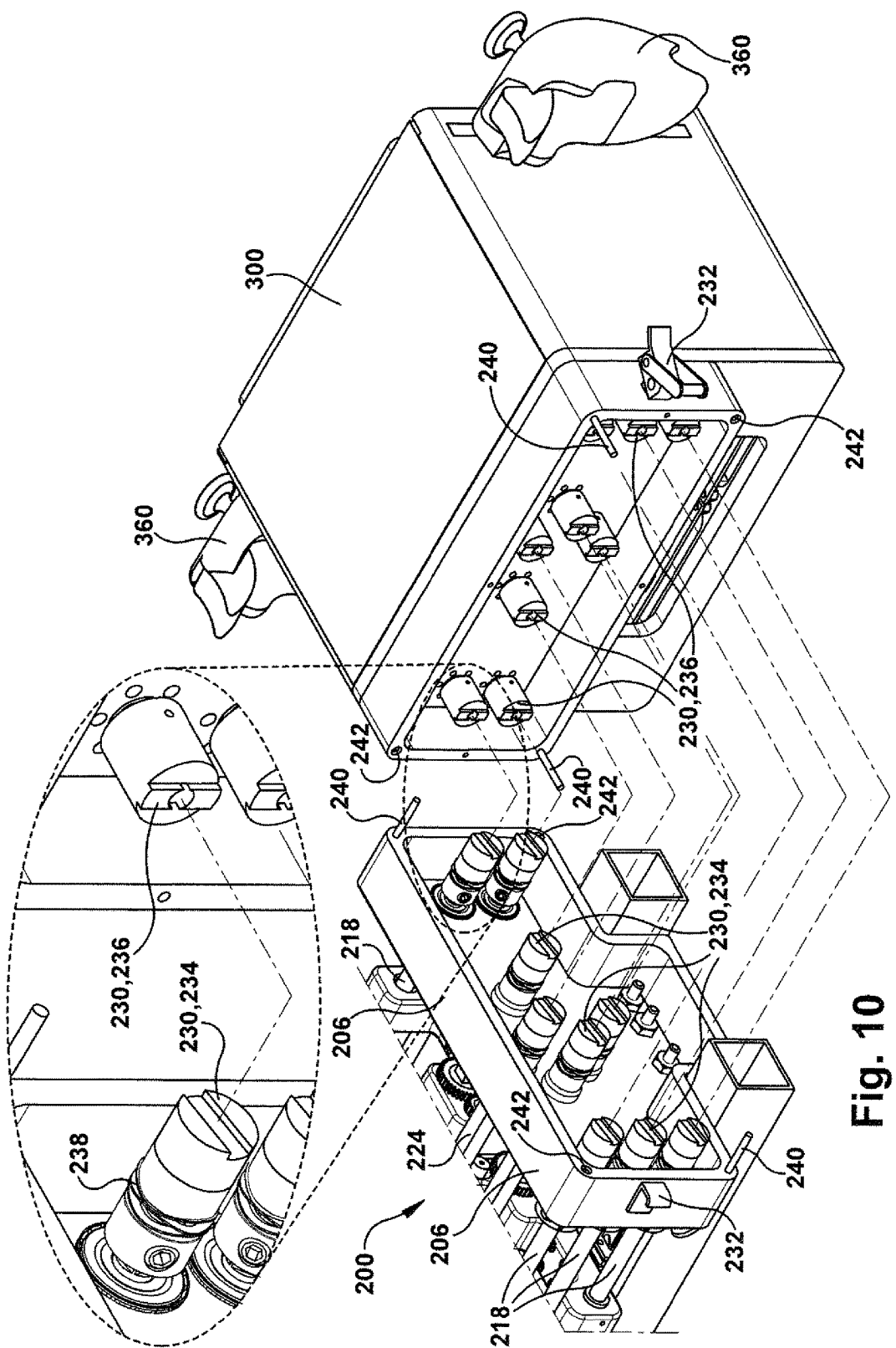
FIG. 10 is an exploded isometric view of a portion of the robot illustrated in FIGS. 2-9 with certain portions magnified for clarity.

Referring to FIG. 10, the motor pack 300 is connectable to the motor interface housing 206 of the transmission 200 by means 232, such as a quick release latch. The motor pack 300 and transmission 200 include pins 240 and corresponding guide holes 242 that mate with each other to guide the motor pack to the correct position on the transmission. The latch 232 is actuatable to lock the transmission 200 and motor pack 300 in this desired position.

Figure 9:
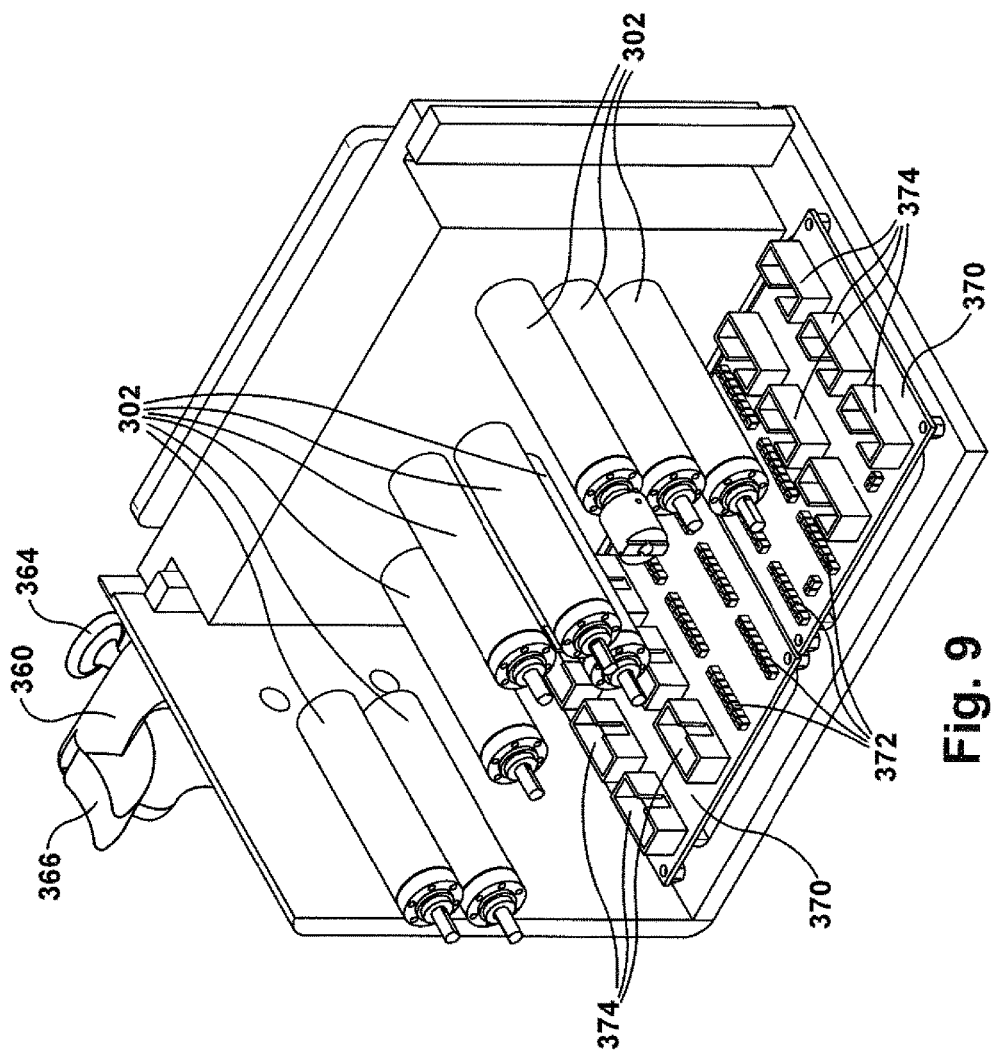
FIG. 9 is an isometric view of a portion of the robot illustrated in FIGS. 2-8, with certain portions removed.

Referring to FIGS. 9 and 10, the motor pack 300 includes motors 302 for imparting rotation to the drive screws 218 and rotation shafts 224. A separate individual motor 302 is provided for each drive screw 218 and rotation shaft 224. Since each drive screw 218 and rotation shaft 224 is associated with one degree of freedom of the robot 20, each motor 302 is also associated with one degree of freedom of the robot. Therefore, the degrees of freedom of the robot 20 can be controlled individually through actuation of the motors 302. It therefore follows that, for the nine DOF robot 20 of the illustrated embodiment, the motor pack 300 includes nine motors 302.

As shown in FIG. 9, the motor pack 300 includes printed circuit boards 370 that include pin sockets 372 for receiving integrated circuit (IC) chips (not shown), such as motor controllers, processors, video controllers, etc., for implementing the control functions of the robot 20 and for communicating with the robot interface PC 60. Wiring sockets 374 receive corresponding cable plugs (not shown) that wire the motors 302 to the circuit boards 370 and also connect the wires of the cable(s) 312 to the circuit boards.

The motors 302 can be of any desired configuration, such as a brushless DC stepper motor configuration. In one example configuration, the motors 302 can be brushless 8 Watt DC motors equipped with 29:1 planetary gear heads. These motors can have a high power to weight ratio in comparison with other motors in their class. The motors 302 are mounted in the motor pack 300 so that they align axially with, and connect automatically to, their corresponding drive screw 218 or rotation shaft 224 when the motor pack 300 is connected to the interface housing 206. This automatic connection is facilitated by couplings 230 that have components connected to the drive screws 218, rotation shafts 224, and motors 302.

In the example illustrated in FIG. 10, the motor couplings 230 are Oldham couplings, which are well known in the art as being shaft couplings that are simple, secure, reliable, and that allow for some misalignment in the shafts. Each coupling 230 includes a female coupler 234 associated with its associated drive screw 218 or rotation shaft 224, and a male coupler 236 associated with its associated motor 302. One or both of the male and female couplers 234, 236 can be movable axially against the bias of a spring. In the embodiment illustrated in FIG. 10, the female coupler 234 is so biased by a wave spring 238.

The female couplers 234 include a slot for receiving a tab of the corresponding male coupler 236 Through the engagement between the tab and slot, the male coupler can transmit rotational force from the associated motor 302 to the associated screw/shaft 218, 224. Since the slot in the female coupler 234 extends laterally through the entire coupler, the tab in the male coupler 236 can slide laterally in the slot and can even protrude partially from the slot. This is the essence of the Oldham coupling design, which allows the couplings 320 to account for lateral misalignments between the motors 302 and screw/shafts 218, 224.

When the motor pack 300 is assembled with the transmission 200, the guide pins 240 and holes 242 guide the motor pack onto the transmission and the latches 232 lock the motor pack onto the transmission. As this occurs, the male couplers 236 on the motor pack 300 move into engagement with the corresponding female couplers 234 on the transmission 200. If the male coupler tabs happen to align with and enter the female coupler slots, the coupling takes place immediately. If not, the female couplers are deflected axially against the bias of the wave spring 238. In the initial set up of the robot 20, the motors 302 can be operated to cause rotation of the male couplers 236, which will bring the male and female couplers into alignment, at which time, the female coupler 234 will move axially under the bias of the wave spring 238 so that the male coupler tab enters the female coupler slot. Through the couplings 230 of the transmission 200 and the quick release latches 232 of the motor pack 300, the motor pack can be attached to the transmission 200 and the motors 302 can be coupled to the screws 218 and shafts 224 in a quick, easy, and reliable manner.

The Robot—Biocompatibility

The endoscope 100, transmission 200, and concentric tube manipulators 150 can be designed to be both sterilizable and biocompatible, constructed entirely from autoclavable and biocompatible components. For example, the materials used to construct these components can be either biocompatible polymers (e.g., Ultem® or PEEK®), stainless steel (which would be passivated before clinical use), aluminum (which would be anodized before clinical use), or nitinol (in the case of the manipulators 150). Certain connections between the components can be achieved using a biocompatible and autoclavable bonding agent or glue (e.g., Loctite®, M-21 HP medical device epoxy agent). All of these materials can withstand sterilization in an autoclave.

Referring to FIG. 1, the robot 20 can incorporate a sterile bag 310 that helps isolate the motor pack 300 from the surgical environment. The sterile bag 310 has an opening sized so that the edges coincide with the dimensions of the engaging surfaces of the motor pack 300 and motor interface housing 206. Thus, when the motor pack 300 is connected to the transmission 200, the sterile bag 310 is clamped in place. To facilitate this connection and promote a sterile barrier, a sterile ring or gasket can be provided between the motor pack 300 and transmission 200. The bag 310 can have openings through which the control handles 350 can extend, and is tied or otherwise drawn closed around robot cabling 312.

With the sterile bag 310 connected as shown in FIG. 1, the male couplings 236 (See FIG. 10) on the motor pack 300 are left exposed so that they can engage and mate with the female couplings 234 on the transmission 200. When the motor pack 300 is connected to the transmission 200, the couplings 230 are positioned in an enclosure formed by the motor pack 300 and the motor interface housing 206. The manner in which the female and male couplings 234, 236 are secured to the transmission 200 and motor pack 300, respectively (e.g., using gaskets, bushings, etc.) creates a tortuous path that helps isolate any non-sterile portions of the couplings 230 from the surgical environment.

To set up the robot 20 in the operating room, the endoscope 100, transmission 200, and concentric tube manipulators 150 are first autoclaved to sterilize the unit. The sterile bag 310 is attached to the motor pack 300, which is then secured to the transmission 200 via the latches 232. The sterile bag 310 is then pulled over the motor pack 300 and sealed using means, such as sterile tape. The motor pack 300 is thereby isolated from the sterilized endoscope 100, transmission 200, and concentric tube manipulators 150.

Procedure Specific Configurations

The robot 20 can be configured to perform certain endoscopic surgical procedures through the configuration of the endoscope tube 106, the concentric tube manipulators 150, and the tools that the manipulators carry. In the illustrated example embodiment, the robot 20 is configured for transurethral treatment of benign prostatic hyperplasia (BPH). In this configuration, the laser 152 carried at the tip 168 of the first concentric tube manipulator 160 is a Holmium laser, which is a type of laser commonly used for tissue ablation. In this particular configuration of the robot 20, the laser 152 is for performing a Holmium laser enucleation of the prostate (HoLEP) procedure. The six DOF configuration of the first concentric tube manipulator 160 provides significant dexterity to the user. The grippers 154 carried at the tip 178 of the second concentric tube manipulator 170 gives the user the ability to manipulate and remove tissue.

According to the illustrated example configuration of the invention, the robot 20, particularly the concentric tube manipulators 150 and the transmission 200, can be adapted to receive and cooperate with a conventional, commercially available endoscope 100. In one example, the endoscope 100 can be a Storz Model 27292 AMA endoscope, which is commercially available from Karl Storz Endovision, Inc. of Charlton, Mass. Advantageously, this endoscope is currently used clinically for prostate surgery, so its ability to be inserted through the urethra to access and operate on the prostate is proven. In this instance, the transmission 200 can include an adapter 250 specifically designed to connect the conventional endoscope to the transmission. As an additional advantage, this endoscope can include integrated optics 180 and light sources 182, which are shown in FIG. 8.

The use of a conventional endoscope in the configuration of the robot 20, however, is not an absolute requirement. For purposes of this description, reference to the endoscope 100 as a portion of the robot 20 should be considered to describe only the inclusion of a tube commensurate with the endoscope tube 106 of the illustrated conventional endoscope. Whether the robot 20 includes a conventional endoscope is not material. For example, in an alternative configuration, the robot 20 could simply include a custom tube, such as a stainless steel tube, that is either permanently fixed to, or connectable to and removable from, the front end of the robot 20. This tube would be configured to have similar or identical dimensions as those of the tube 106 of endoscope 100. This configuration would eliminate the inclusion and associated costs of the commercially available conventional endoscope from the robot 20.

For instance, the robot 20 could be fit with a tube similar or identical to the endoscope tube 106 of the illustrated endoscope 100, only without the remainder of the endoscope components. In this case, the robot 20 would be fit with the optics 180 and light source(s) 182. Separate ports for optics/light cabling and the introduction of fluids or other media could also be included in this alternative configuration. In one particular example, spacer 156 can support the concentric tube manipulators 150, the optics 180, and the light sources 182 in the inner lumen 102 of the endoscope tube 106.

Additionally, the endoscope tube 106 does not necessarily have a rigid tube construction. The endoscope tube 106 can have a flexible construction that allows for its insertion and delivery along a non-linear or curved path. The flexible tube 106 can be bent or otherwise manipulated by the surgeon to a desired shape calculated to deliver the concentric tube manipulators 150 along a desired path. The concentric tube manipulators 150 will conform to the shape of the tube 106. To facilitate this construction, the concentric tube manipulators 150 would need to be flexible. The superelastic, nitinol construction of the concentric tubes advantageously accommodates this requirement.

The endoscope tube 106 can be sized commensurate with the surgical procedure for which it is intended. Generally speaking, endoscopic procedures can implement an endoscope tube having an outside diameter (O.D.) of about 2-20 mm. Incisions larger than this can begin to reduce the benefit of the minimally invasive approach. For instance, neuroendoscopes can be only a few millimeters in diameter. A bronchoscope can typically be about 4 mm at the tip, but some can be smaller. Colonoscopes are typically 10 mm in diameter or a few millimeters larger. Abdominal endoscopes can be 10-12 mm in diameter, and up to 20 mm in the case of a single port through the navel. Advantageously, if the incision is 3 mm or less, suturing is not necessary.

Since nitinol tubes are available with an outer diameter of as little as 200 μm or less, the robot 20 with endoscope tubes 106 having an O.D. as small as 2 mm or potentially less, and carrying two or more concentric tube manipulators 150 can be produced. As the endoscope tube 106 increases in diameter, the diameter of the concentric tube manipulators 150 that can be implemented in the robot 20 also increases. Additionally, as the diameter of the endoscope tube 106 increases, the number of concentric tube manipulators 150 implemented in the robot 20 also increases. Increasing the number of concentric tube manipulators 150 would, of course, increase the size and complexity of the transmission 200 and motor pack 300. Following these guidelines, the selection of the diameter of the endoscope tube 106 can be commensurate with the procedure being performed and the physiological limitations associated with that procedure.

For instance, with regard to the transurethral implementation described in the example embodiments herein, the endoscope 100 can be a 26 FR endoscope, which corresponds to an endoscope tube 106 having an O.D. of 8.66 mm. Endoscopes of this diameter are known to be effective in performing transurethral procedures. The optics 180 and light sources 182 occupy a generally crescent shaped, semicircular portion of the inner lumen 102 of the endoscope tube 106. This leaves about half the inner lumen 102, having a maximum width of about 8 mm and a height of about 4 mm as the space in which to implement the concentric tube manipulators 150. This space is ample to permit the use of concentric tube manipulators 150 each having an O.D. of up to slightly above 2 mm.

As shown in FIG. 8, the manipulators 150 along with the spacer 156 fit easily into the inner lumen 102, leaving ample space for defining a delivery channel in the endoscope tube 106. The delivery channel defined by the inner lumen 102 can be used to supply an irrigation fluid to the worksite, a distension or insufflation fluid to the worksite, or any other desired solid, liquid or gaseous media to the worksite. For example, surgical procedures of the urethra, bladder, prostate, kidney, etc, typically can involve the use of a liquid, i.e., saline solution, to distend the tissue at the worksite in order to provide space for viewing and for maneuvering the manipulators 150. Similarly, surgical procedures in the abdomen or chest typically can involve the use of a gas, such as air, carbon dioxide, or helium, to distend or insufflate the tissue at the worksite in order to provide space for viewing and for maneuvering the manipulators 150. Advantageously, the endoscope 100 of the robot 20 can be configured so that the inner lumen 102 of the endoscope tube 106 defines the delivery port or channel. As an additional feature, the spacer 156 can include a portion that serves as a nozzle for directing the media delivered via the channel of the inner lumen 102.

A robot 20 comprising two or more concentric tube manipulators 150 in an endoscope tube 106 that can access the prostate transurethrally is an unprecedented construction. This is especially true given the fact that the endoscope tube 106 also includes the integrated optics 180, light sources 182, and delivery channel. The average male urethra is about 6.0 mm in diameter. The transurethral aspect of the delivery method limits the O.D. of the endoscope tube 106 to slightly greater than 6.0 mm due to the ability of the tissue surrounding the urethra to stretch. The endoscope tube 106 implemented in the robot 20 of the present invention provides all of the functionality described herein in an endoscope tube having an O.D. 26 Fr (8.66 mm), which is about as large as the urethra can accept, given its ability to stretch.

Quantifying the advantages of this construction in a transurethral implementation, the robot 20 of the present invention can provide two or more robotically actuated concentric tube manipulators 150 in an endoscope tube 106 that can be delivered transurethrally and that is equipped with optics 180, light sources 182, and a delivery channel, wherein the ratio of endoscope tube diameter to concentric tube manipulator diameter is at least 2:1. (In this description, the diameter of the concentric manipulators is considered the O.D. of the largest, i.e., outer, tube.) In fact, depending on factors such as the desired dexterity of the concentric tube manipulator 150 and the size and type of surgical tool carried by the manipulator, the ratio of endoscope tube diameter to concentric tube manipulator diameter can be at least 3:1 or more.

Other implementations produce similar advantageous constructions. For example, transnasal skull-based surgery can be used to resect the pituitary gland in order to remove a tumor. In this procedure, the nostril is the natural orifice, which has an opening that is about 16 mm by 35 mm. From there, a passage extends about 100 mm and widens as it approaches the pituitary gland. The size of the sella turcica (the chamber holding the pituitary gland), however, is a comparatively small roughly ellipsoidal space with an 8.5 mm major radius and a 6 mm minor radius. Advantageously, the robot 20 of the present invention can be configured with an endoscope tube 106 sized for accommodation in the space leading to the sella turcica. This endoscope tube 106 can deliver two or more concentric tube manipulators 150 sized and configured to operate within the confines of the sella turcica in order to perform the surgical procedure. Thus, in this scenario, since the endoscope tube 106 can be larger, the ratio of endoscope tube diameter to concentric tube manipulator diameter can be at least 3:1, or significantly higher.

As another example, a transoral surgical procedure can be used to perform a pulmonary surgical operation. In this implementation, the natural orifice is the throat. The radius of the bronchi is the limiting factor in determining the size of the endoscope tube 106. The size of the endoscope tube 106 depends on the requisite degree of penetration into the bronchi. Since the bronchi branch off and narrow, a flexible endoscope tube 106 could facilitate further delivery of the concentric tube manipulators 150. From there, the concentric tube manipulators 150 can be deployed to perform the procedure. Advantageously, for deep lung penetration, the robot 20 can be configured to implement an endoscope tube on the small end of the range, such as about 3 mm. Even in these small diameter configurations, the ratio of endoscope tube diameter to concentric tube manipulator diameter can be 2:1 or higher.

Typical transanal or transabdominal endoscopic procedures typically use endoscopes in the range of 10-12 mm in diameter or larger. The robot 20 can be configured with a similarly sized endoscope tube 106 for these procedures. Due, however, to the compact size of the concentric tube manipulators 150, using the robot 20 of the present invention to perform these procedures can potentially reduce the requisite size of the endoscope tubes 106. While perhaps not as significant in the transanal procedure due to the luxury of space in this natural orifice procedure, this can be of tremendous benefit in performing transabdominal procedures because a reduction in scope size yields a reduction in the size of the abdominal incision.

Operating the Robot

Regardless of the surgical procedure, the robot 20, supported by the support device 30, can be maneuvered manually by the surgeon with ease due to the counterbalancing features of the support device. These counterbalancing features can even be configured to suit the surgeon's preferences by incorporating variable damping into the support device. To perform operations with coarse control, the surgeon can maneuver the entire robot 20 manually in order to maneuver the endoscope tube 106. An example of a coarse control function may be to insert the endoscope tube 106 through the urethra under the guidance of the imaging (i.e., ultrasound) equipment 50. These coarse movements of the robot 20 facilitate positioning the distal end 104 of the endoscope 100 at the desired worksite (e.g., the prostate) in the patient 12. Once the coarse positioning is complete, if the surgeon chooses, the support device 30 can be locked to fix the position of the robot 20 relative to the patient 12 so that fine control can be implemented as described below.

Fine control of the robot 20 can be achieved through the robotic operation of the concentric tube manipulators 150. The surgeon can control the manipulators 150 through the user interface and control features 350 included with the motor pack 300. These features 350 include a display panel 352 mounted on a rear facing portion of the motor pack 300 in combination with a pair of control handles 360 mounted on opposite sides of the motor pack 300. Each control handle 360 is associated with a corresponding one of the manipulators 150. The motor pack 300 can also include one or more pushbuttons 354 for accessing menu-driven features, such different operating modes, system setup, calibration routines, etc.

Each control handle 360 has an ergonomically contoured handle portion 362 that facilitates a comfortable and natural feel when grasped. Each control handle 360 also includes a thumb joystick 364 with pushbutton capability, as well as an index finger trigger 366. The trigger 366 has a configuration that allows for sensing the degree to which the trigger is actuated. For example, the trigger 366 can have an analog configuration, such as a variable resistance configuration, and can provide a percent actuated (e.g., 0-100%) indication of its degree of actuation.

Advantageously, the handle portions 362 have a robust configuration so that they can be grasped and used to manipulate the robot 20 for coarse control, while simultaneously allowing for fine control of the concentric tube manipulators 150 through use of the joystick 364 and trigger 366. In this manner, the surgeon can employ the robot 20 in a manner suited to his preferences and in response to different operating scenarios. For instance, the surgeon may prefer to locate the distal end 104 of the endoscope 100 at the work site through manual coarse operation of the robot 20. In doing so, the surgeon may prefer to manually lock the position of the robot 20 via the support device 30 to fix the distal end 104 of the endoscope 100 at the worksite in the patient 12. The enables the surgeon to perform fine control of the robot 20, i.e., the manipulators 150, through actuation of the joystick 364 and/or trigger 366.

Alternatively, the surgeon may choose to leave the support device 30 unlocked so as to allow for performing both coarse and fine operations simultaneously or in combination with each other. As another alternative, two or more surgeons can operate the robot simultaneously, with one surgeon being responsible for coarse manual control and one surgeon being responsible for fine robotic control.

As a further example, instead of being mounted on the support device 30, the robot 20 itself could be mounted on a robotic arm, such a robotic arm of Intuitive Surgical, Inc.'s da Vinci™ Surgical System described above. In this instance, coarse control of the robot 20 could be implemented through operation of the robot arm, and fine control could be implemented via operation of the robot 20 itself. In this alternative implementation, control handles similar or identical to those positioned on the motor pack 300 can be positioned remotely, at or near the robot arm controls so that both the robot arm and the robot 20 can be controlled from the same location.

The joystick 364 and trigger 366 can be configured to control operation of the concentric tube manipulators 150 in a variety of manners. In an example configuration, digital and/or analog signals from the joystick 364 and trigger 366 can be mapped to velocities of the tip of the associated concentric tube manipulator 150 with respect to the distal end 104 of the endoscope tube 106. For each controller 360, the trigger 366 can be mapped to the axial insertion direction of the manipulator 150 and the two degrees of freedom of the joystick 364 were mapped to the lateral directions. To change the direction of axial motion (insertion vs. retraction) controlled by the trigger 366, the surgeon presses the push button of the joystick 364.

Figure 11:
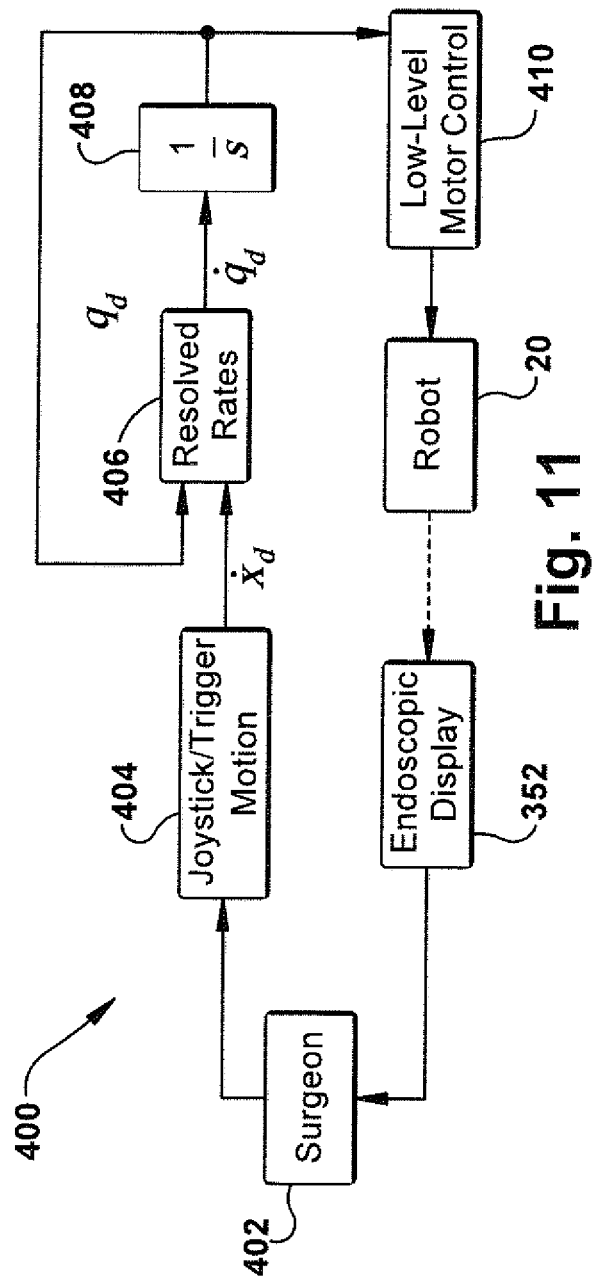
FIG. 11 is a block diagram illustrating the operation of the system and apparatus illustrated in FIG. 1 and the robot illustrated in FIGS. 2-10.

Real-time control is implemented using known control software, such as xPC Target® and Simulink® software (available commercially from MathWorks, Inc. of Natick, Mass.). A block diagram of the control interface 400 is shown in FIG. 11. As shown in FIG. 11, the surgeon 402 specifies a desired velocity in task space via displacement of the trigger 366 and joystick 364. The desired velocity ($\dot{X}_d$) is converted into a desired joint space velocity ($\dot{q}_d$) using a resolved rates algorithm 406 implementing a kinematics model. These velocities are then integrated at 408 to obtain desired joint positions ($q_d$), which are used for low-level control 410 of the robot 20, i.e., of the motors 302 that operate the concentric tube manipulators 150. The surgeon 402 can view the resulting motion of the manipulators 150 on the display 352, which provides the feedback necessary to allow him/her to operate the robot 20 to perform the desired task.

For the illustrated example embodiment, the kinematic models implemented in the resolved rates algorithm 406 are based on the number of tubes (e.g., two, three, etc.) which determines the degrees of freedom (e.g., three, six, etc.) of the concentric tube manipulator 150. Kinematic models for the two and three concentric tube manipulators of the illustrated example embodiment are described below. Those skilled in the art will appreciate that concentric tube manipulators having additional numbers of tubes would necessitate kinematic models to account for their additional degrees of freedom.

Kinematics of the Three Tube Manipulator

For the six DOF first concentric tube manipulator 160, the forward kinematics are solved via the model described in D. C. Rucker et al, A geometrically exact model for externally loaded concentric-tube continuum robots," *IEEE Transactions on Robotics*, vol. 26, no. 5, pp. 769-780, 2010, which is hereby incorporated by reference in its entirety. The Jacobian is computed according to D. C. Rucker et al. "Computing Jacobians and compliance matrices for externally loaded continuum robots," *IEEE International Conference on Robotics and Automation*, pp. 945-950, 2011, which is hereby incorporated by reference in its entirety. These models are implemented in C++ and sent via user datagram protocol (UDP) to the main controller in Simulink. The six DOF manipulator also requires the implementation of a redundancy resolution algorithm since only the three DOF tip position is to be controlled. Under one approach, redundancy can be resolved by locally minimizing joint speeds. Alternative redundancy resolution approaches could be implemented.

Kinematics of the Two Tube Manipulator

For the three DOF second concentric tube manipulator 170, the forward kinematics and hybrid Jacobian can be calculated in closed form in the following manner. The forward kinematics of the two-tube robot with a straight outer tube and a constant curvature inner tube can be written in closed form. Here, it is assumed that the outer tube is sufficiently stiff that the inner tube does not bend it significantly. The inner tube is elastic with constant precurvature $\kappa$. The actuation variables are $a_1$, which denotes the angular position of the inner tube, $\beta_1 \in s$ (where s measures arc length), which is the location where the inner tube is held by its carrier, and $\beta_2 \in s$, which is the location where the outer straight tube is held by its carrier. We define s=0 to be where the manipulators 150 exit the distal end 104 of the endoscope tube 106, with positive s toward the prostate. Further, let us define $l_1$ and $l_2$ to be the physical lengths of the tubes. Consider a fixed frame at the tip of the endoscope 100, with its z-axis tangent to the endoscopic axis, and its x-axis defined as the direction about which the inner tube curves at $a_1$=0. Let us also place a body frame at the tip of the robot with its z-axis tangent to the central axis of the robot at its tip, and its x-axis in the direction about which the tube curves (note that the body frame moves with the robot's tip as the robot deforms). Using these definitions, the forward kinematics, $g_{st}$, is given by:

$$g_{st} = \begin{bmatrix} R & d \\ 0 & 1 \end{bmatrix} \quad \text{(Eq. 1)}$$

$$R = \begin{bmatrix} c_{\alpha_1} & -s_{\alpha_1}c_\gamma & s_{\alpha_1}s_\gamma \\ s_{\alpha_1} & c_{\alpha_1}c_\gamma & -c_{\alpha_1}s_\gamma \\ 0 & s_\gamma & c_\gamma \end{bmatrix}$$

$$d = \begin{bmatrix} -rs_{\alpha_1}(c_\gamma - 1) \\ rc_{\alpha_1}(c_\gamma - 1) \\ l_2 + \beta_2 + rs_\gamma \end{bmatrix}$$

where $\gamma = \kappa(\beta_1 - \beta_2 + l_1 - l_2)$ and $r = 1/\kappa$. The spatial Jacobian $J_s$ can be defined from the forward kinematics as:

$$J_s = \left[ \left(\frac{\partial g_{st}}{\partial \alpha_1} g_{st}^{-1}\right)^V \; \left(\frac{\partial g_{st}}{\partial \beta_1} g_{st}^{-1}\right)^V \; \left(\frac{\partial g_{st}}{\partial \beta_2} g_{st}^{-1}\right)^V \right] \quad \text{(Eq. 2)}$$

The relationships between the spatial, body, and hybrid Jacobians are defined as:

$$J_s = Ad_{g_{st}} J_b \quad \text{(Eq. 3)}$$

$$J_h = \begin{bmatrix} R & 0 \\ 0 & R \end{bmatrix} J_b$$

where $Ad_{g_{st}}$ is the adjoint transformation, $J_h$ is the hybrid Jacobian, and $J_b$ is the body Jacobian. Using Equations 1 and 3, the hybrid Jacobian can be shown to be:

$$J_h = \begin{bmatrix} rc_{\alpha_1}(1 - c_\gamma) & s_{\alpha_1}s_\gamma & -s_{\alpha_1}s_\gamma \\ rs_{\alpha_1}(1 - c_\gamma) & -s_\gamma c_{\alpha_1} & s_\gamma c_{\alpha_1} \\ 0 & c_\gamma & 1 - c_\gamma \\ 0 & \kappa c_{\alpha_1} & -\kappa c_{\alpha_1} \\ 0 & \kappa s_{\alpha_1} & -\kappa s_{\alpha_1} \\ 1 & 0 & 0 \end{bmatrix} \quad \text{(Eq. 4)}$$

Using this Jacobian, a singularity robust resolved rates algorithm is implemented. The update step in this algorithm is given as:

$$\dot{q} = (J_h^T J_h + \lambda^2 I)^{-1} J_h^T \dot{x} \quad \text{(Eq. 5)}$$

where $\lambda^2$ is given by:

$$\lambda_2 = \begin{cases} 0, & \sigma_m \geq \varepsilon \\ \left(1 - \frac{\sigma_m^2}{\varepsilon}\right) \lambda_{max}^2, & \sigma_m < \varepsilon \end{cases} \quad \text{(Eq. 6)}$$

where $\varepsilon$ determines how close to singularity one wishes the system to be before implementing the damping factor, $\lambda_{max}$ is the maximum damping factor, and $\sigma_m$ is the minimum singular value of $J_h$, which indicates the degree to which the Jacobian is conditioned.

Experimental Testing

The robot 20 of the present invention allows the surgeon to reduce or minimize the degree to which he relies on maneuvering the endoscope 100 itself from outside the patient in order to perform the HoLEP procedure. The surgeon can insert the endoscope 100 to position the distal end 104 of the endoscope tube 106 at the worksite (i.e., the prostate and the intrapelvic space surrounding the prostate). From this position, the surgeon can use the concentric tube manipulators 160, 170 to maneuver the laser 152 and grippers 154 locally at the worksite instead of maneuvering the entire robot 20 and endoscope 100 from outside the patient. Advantageously, this can reduce the angle that the surgeon must apply to the endoscope 100 during surgery, which reduces the force that the surgeon must apply to perform the procedure. This can help reduce both the physical demands placed on the surgeon and the trauma applied to the patient.

Figure 12:
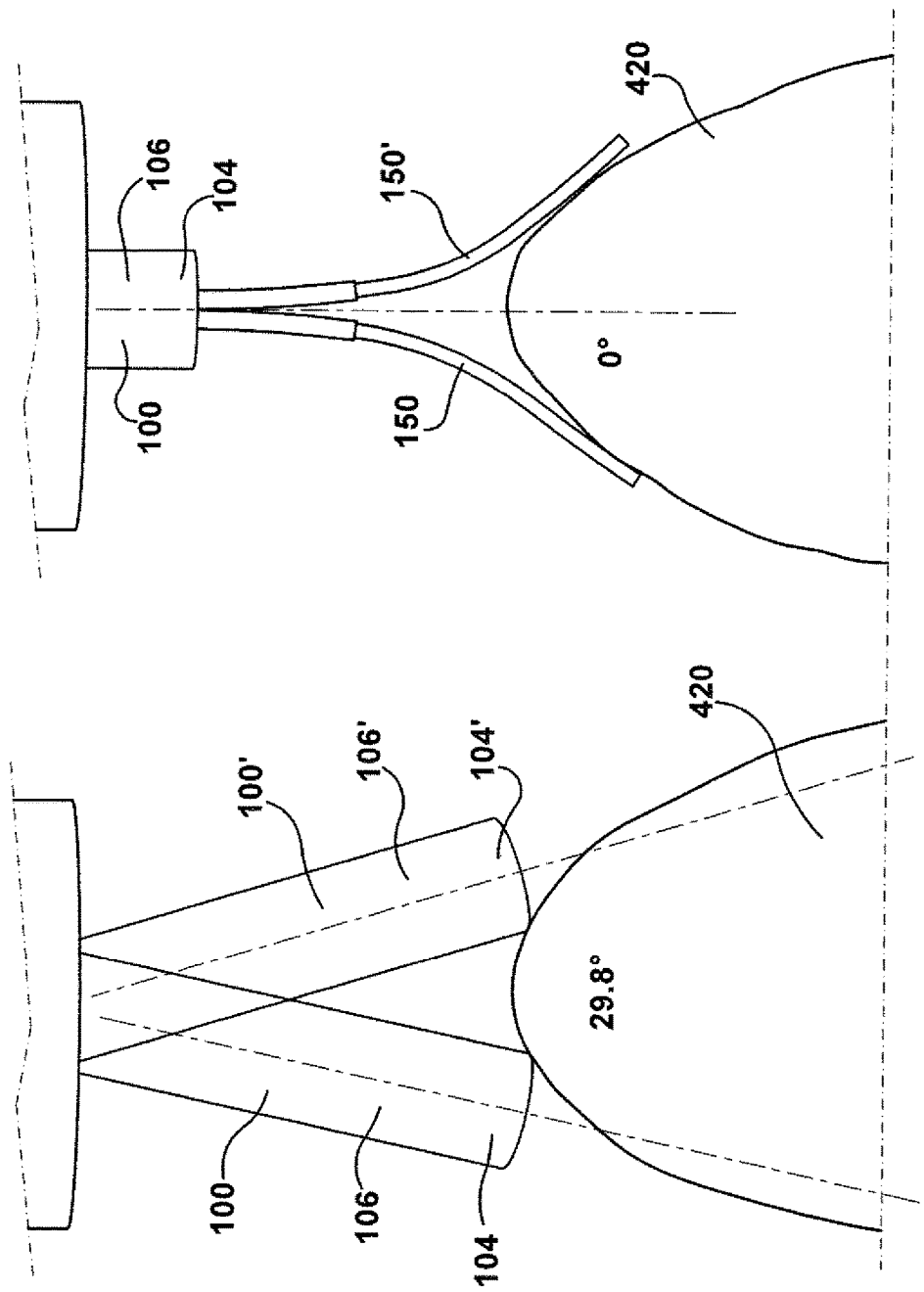
FIG. 12 is a schematic illustration comparing the function of the system and apparatus illustrated in FIG. 1 and the robot illustrated in FIGS. 2-11 to the function of a conventional endoscope.

To illustrate this point, referring to FIG. 12, an ellipsoid 420 representative of a prostate is accessed by an endoscope 100. On the left as viewed in FIG. 12, it can be seen that the endoscope 100 has to be maneuvered almost 30 degrees in order for the distal end 104 of the endoscope tube 106 to access the peripheral regions of the prostate 420. These positions would correspond to those available through coarse manual movements of the robot 20. Such extreme coarse manual movements can be physically taxing on the surgeon and can cause trauma to the patient 12.

Advantageously, as viewed on the right in FIG. 12, the tip of the concentric tube manipulator 150 delivered by the endoscope 100 can access the peripheral regions of the prostate 420 without maneuvering the endoscope at all. It can thus be seen that the robot 20 of the present invention offers several improvements to HoLEP surgery. Using the robot 20 can make HoLEP surgery easier to perform and can reduce the time required to perform the procedure. The robot 20 can achieve this by enhancing dexterity at the worksite while at the same time minimizing the surgeons physical effort and the amount of trauma placed on the patient. It will thus be appreciated that, through a combination of coarse manual control and fine robotic control, the robot can provide maximal surgical access to the prostate 420.

From the above description of the invention, those skilled in the art will perceive improvements, changes and modifications. Such improvements, changes and modifications within the skill of the art are intended to be covered by the appended claims.

What is claimed is:

1. An apparatus for performing endoscopic surgery on a patient, the apparatus comprising:
   a transmission;
   an endoscope tube connected to and extending from the transmission;
   at least two concentric tube manipulators connected to the transmission and extending adjacent to each other at least partially through the endoscope tube, wherein each of the at least two concentric tube manipulators comprises a plurality of nested tubes arranged concentrically along a manipulator axis and being configured for at least one of rotational movement about the manipulator axis and translational movement along the manipulator axis, wherein at least one of the nested tubes has a pre-curved portion, and wherein, for each manipulator, at least one of the nested tubes is configured to assume a pre-curved configuration when extended relative to at least one of the remaining nested tubes and to deflect when retracted relative to the at least one of the remaining nested tubes;
   a motor pack detachably connected to the transmission and comprising motors operable to impart rotation to at least one shaft of the transmission, the control input device and a controller for controlling operation of the motors, wherein the handles are configured for manually imparting gross physical movements of the apparatus as a whole, and wherein the controller is operative to receive from the at least one manually actuatable control input device control signals indicative of desired movements of surgical tools disposed at distal ends of the at least two concentric tube manipulators, the controller being operative to control operation of the motors in order to produce the desired movements of the surgical tools by actuating the motors to cause the transmission to translate and/or rotate the nested tubes of the at least one concentric tube manipulator;

wherein the transmission is configured to impart the at least one of rotational movement along the manipulator axis and the translational movement along the manipulator axis to the nested tubes of each of the at least two concentric tube manipulators in response to operation of the motors, the apparatus further comprising at least one manually actuatable control input device and a controller for controlling operation of the motors, wherein the controller is operative to receive from the at least one manually actuatable control input device control signals indicative of desired movements of the at least two concentric tube manipulators, the controller being further operative to control operation of the motors in order to produce via the transmission the at least one of rotational movement along the manipulator axis and the translational movement along the manipulator axis that will produce the desired movements of the at least two concentric tube manipulators;

wherein the transmission, motors, endoscope tube, and at least two concentric tube manipulators when assembled form a robot assembly, the apparatus further comprising a support device that supports the robot assembly and facilitates gross maneuvering and positioning of the robot assembly as a whole, the support device being operable to support the robot assembly at a position and orientation that positions the endoscope tube so as to permit operation of the at least two concentric tube manipulators to perform fine operations from a distal end of the fixed endoscope tube robotically as commanded via the at least one manually actuatable control input device.

2. The apparatus recited in claim 1, wherein the at least one manually actuatable control input device comprises at least one of a joystick, pushbutton, and a trigger that are actuatable to provide control signals.

3. The apparatus recited in claim 2, wherein the joystick is actuatable to supply a lateral movement component of the control signal for an associated one of the at least two concentric tube manipulators and the trigger is actuatable to supply an insertion and retraction component of the control signal for the associated one of the at least two concentric tube manipulators.

4. The apparatus recited in claim 1, further comprising optics and a light source positioned in an inner lumen of the endoscope tube at the distal end of the endoscope tube, the light source being operable to illuminate a workspace of the at least two concentric tube manipulators, and the optics being operable to provide video of the workspace.

5. The apparatus recited in claim 1, wherein an inner lumen of the endoscope defines a delivery channel for delivering media to a worksite.

6. The apparatus recited in claim 1, further comprising a spacer fixed in an inner lumen of the endoscope tube at the distal end of the endoscope tube, the spacer being configured to support the at least two concentric tube manipulators in the endoscope tube and guide the at least two concentric tube manipulators from the distal end of the endoscope tube.

7. The apparatus recited in claim 6, wherein the spacer comprises a nozzle for directing fluids from the distal end of the endoscope tube.

8. The apparatus recited in claim 6, wherein the spacer is adapted to support optics and a light source at the distal end of the endoscope tube, the light source being operable to illuminate a workspace of the at least two concentric tube manipulators and the optics being operable to provide video of the workspace.

9. The apparatus recited in claim 1, further comprising a motor pack connected to the transmission, the motor pack comprising the motors, wherein each motor is operable to control one degree of freedom of one of the tubes of the at least two concentric tube manipulators.

10. The apparatus recited in claim 1, wherein the transmission comprises a plurality of tube carriers each of which carry one tube of one of the at least two concentric tube manipulators, each tube carrier having an associated drive screw and rotation shaft, each drive screw being coupled to an associated motor that is operable to rotate the drive screw to cause longitudinal translation of the tube carrier and its associated tube, each rotation shaft being coupled to an associated motor that is operable to rotate the rotation shaft to cause rotation of its associated tube within the tube carrier.

11. The apparatus recited in claim 1, wherein the endoscope tube comprises a portion of a conventional endoscope, and wherein the transmission comprises an adapter for connecting the endoscope to the transmission.

12. The apparatus recited in claim 1, wherein the endoscope tube has an outside diameter of 6.0 mm or less, and a ratio of the outside diameter of the endoscope tube to an outside diameter of the at least two concentric tube manipulators is at least 2:1.

13. The apparatus recited in claim 1, wherein the endoscope tube has an outside diameter of 6.0 mm or less, and a ratio of the outside diameter of the endoscope tube to an outside diameter of the at least two concentric tube manipulators is at least 3:1.

14. The apparatus recited in claim 1, wherein at least one of the at least two concentric tube manipulators carries a laser at its distal tip.

15. The apparatus recited in claim 1, wherein the at least two concentric tube manipulators comprises:
a first concentric tube manipulator that carries a laser at its distal tip; and
a second concentric tube manipulator that carries a gripper mechanism at its distal tip.

16. The apparatus recited in claim 15, wherein the first concentric tube manipulator comprises three concentric tubes having six degrees of freedom, and the second concentric tube manipulator comprises two concentric tubes having three degrees of freedom.

17. The apparatus recited in claim 1, wherein each of the at least two concentric tube manipulators comprise at least one of two concentric tubes having three degrees of freedom, and three concentric tubes having six degrees of freedom.

18. The apparatus recited in claim 1, wherein the endoscope tube comprises a transurethral endoscope tube for delivering the at least two concentric tube manipulators transurethrally to a worksite in the patient.

19. The apparatus recited in claim 1, wherein an outside diameter of the endoscope tube is less than about 20 mm and a ratio of endoscope tube outside diameter to diameters of the at least two concentric tube manipulators is at least 2:1.

20. The apparatus recited in claim 1, wherein an outside diameter of the endoscope tube is less than about 12 mm and a ratio of endoscope tube outside diameter to diameters of the at least two concentric tube manipulators is at least 2:1.

21. The apparatus recited in claim 1, wherein an outside diameter of the endoscope tube is less than about 9 mm and a ratio of endoscope tube outside diameter to diameters of the at least two concentric tube manipulators is at least 2:1.

22. The apparatus recited in claim 1, wherein an outside diameter of the endoscope tube is less than about 3 mm and a ratio of endoscope tube outside diameter to diameters of the at least two concentric tube manipulators is at least 2:1.

23. An apparatus for performing endoscopic surgery on a patient, the apparatus comprising:
  a transmission;
  motors operatively connected to the transmission;
  endoscope tube connected to and extending from the transmission;
  at least two concentric tube manipulators connected to the transmission and extending at least partially through the endoscope tube, wherein each of the at least two concentric tube manipulators comprises a plurality of nested tubes arranged concentrically along a manipulator axis and being configured for at least one of rotational movement about the manipulator axis and translational movement along the manipulator axis, wherein at least one of the nested tubes has a pre-curved portion, and wherein, for each manipulator, at least one of the nested tubes is configured to assume a pre-curved configuration when extended relative to at least one of the remaining nested tubes and to deflect when retracted relative to the at least one of the remaining nested tubes;
  wherein the transmission is configured to impart the rotational movement and/or translational movement to the nested tubes of the at least two concentric tube manipulators in response to operation of the motors, the apparatus further comprising at least one manually actuatable control input device and a controller for controlling operation of the motors, wherein the controller is operative to receive from the at least one manually actuatable control input device control signals indicative of desired movements of the at least one concentric tube manipulator, the controller being further operative to control operation of the motors in order to rotate and/or translate the nested tubes in a manner that will produce the desired movements;
  the apparatus further comprising a motor pack detachably connectable with the transmission and including the motors and controller, the motor pack comprising motor coupling components configured to engage and mate with corresponding coupling components of the transmission when the motor pack is connected to the transmission, wherein the motor pack further comprises handles for manually imparting gross physical movements of the apparatus as a whole, and wherein the at least one manually actuatable control input device is included on the handles and configured so that the operator can control robotic movement of the at least two concentric tube manipulators while grasping the handles.

24. An apparatus for performing endoscopic surgery on a patient, the apparatus comprising:
  a transmission;
  motors operatively connected to the transmission;
  an endoscope tube connected to and extending from the transmission;
  at least two concentric tube manipulators connected to the transmission and extending at least partially through the endoscope tube, wherein each of the at least two concentric tube manipulators comprises a plurality of nested tubes arranged concentrically along a manipulator axis and being configured for at least one of rotational movement about the manipulator axis and translational movement along the manipulator axis, wherein at least one of the nested tubes has a pre-curved portion, and wherein, for each manipulator, at least one of the nested tubes is configured to assume a pre-curved configuration when extended relative to at least one of the remaining nested tubes and to deflect when retracted relative to the at least one of the remaining nested tubes;
  wherein the transmission is configured to impart the rotational movement and/or translational movement to the nested tubes of the at least one concentric tube manipulator in response to operation of the motors, the apparatus further comprising at least one manually actuatable control input device and a controller for controlling operation of the motors, wherein the controller is operative to receive from the at least one manually actuatable control input device control signals indicative of desired movements of the at least two concentric tube manipulators, the controller being further operative to control operation of the motors in order to rotate and/or translate the nested tubes in a manner that will produce the desired movements;
  the apparatus further comprising a motor pack detachably connectable with the transmission and including the motors and controller, the motor pack comprising motor coupling components configured to engage and mate with corresponding coupling components of the transmission when the motor pack is connected to the transmission;
  the apparatus further comprising a camera disposed at a distal end of the endoscope, wherein the motor pack further comprises a display screen positioned on a proximal end of the motor pack, the display screen being configured to display to the user a surgical worksite in the area of the distal end of the endoscope.

25. An apparatus for performing endoscopic surgery on a patient, the apparatus comprising:
  a transmission;
  an endoscope tube connected to and extending from the transmission;
  at least two concentric tube manipulators connected to the transmission and extending at least partially through the endoscope tube, wherein each of the at least two concentric tube manipulators comprises a plurality of nested tubes at least one of which having a portion with a pre-curved elastic construction, each of the at least two concentric tube manipulators further comprising a surgical tool fixed to a distal tip of one of the nested tubes of each of the at least two concentric tube manipulators; and
  a motor pack detachably connected to the transmission and comprising motors operable to impart rotation to at least one shaft of the transmission, the motor pack further comprising handles including at least one manually actuatable control input device and a controller for controlling operation of the motors, wherein the handles are configured for manually imparting gross physical movements of the apparatus as a whole, and wherein the controller is operative to receive from the at least one manually actuatable control input device control signals indicative of desired movements of the surgical tools, the controller being operative to control operation of the motors in order to produce the desired movements of the surgical tools by actuating the motors to cause the transmission to translate and/or rotate the nested tubes of the at least one concentric tube manipulator.

* * * * *